United States Patent [19]

Hood et al.

[11] Patent Number: 4,704,256
[45] Date of Patent: Nov. 3, 1987

[54] APPARATUS FOR THE SEQUENTIAL PERFORMANCE OF CHEMICAL PROCESSES

[75] Inventors: Leroy E. Hood, Pasadena; Michael W. Hunkapiller, San Gabriel; William J. Dreyer, Pasadena; Rodney M. Hewick, Pasadena; Anton W. Stark, Pasadena, all of Calif.

[73] Assignee: California Institute of Technology, Pasadena, Calif.

[21] Appl. No.: 440,571

[22] Filed: Nov. 10, 1982

Related U.S. Application Data

[63] Continuation of Ser. No. 190,100, Sep. 23, 1980, abandoned.

[51] Int. Cl.$^4$ .............................................. G01N 33/68
[52] U.S. Cl. ...................................... 422/68; 422/81; 436/89
[58] Field of Search .............. 137/DIG. 8; 210/500.2, 210/282; 239/524, 267; 251/61.1; 422/56, 58, 59, 66, 68, 81, 101, 103, 241, 190, 211, 50; 436/89, 177, 178, 174

[56] References Cited

U.S. PATENT DOCUMENTS

| | | | |
|---|---|---|---|
| 2,136,170 | 11/1938 | Luertzing | 422/101 X |
| 2,721,788 | 10/1955 | Schad | 422/190 |
| 2,789,654 | 4/1957 | Zurit | 210/282 X |
| 3,312,634 | 4/1967 | Bernas et al. | 422/190 X |
| 3,645,689 | 2/1972 | Sjoquist | 436/89 |
| 3,650,132 | 8/1953 | Reinecke | 239/567 |
| 3,865,728 | 2/1975 | Abbott et al. | 210/508 X |
| 3,879,127 | 4/1975 | Storr et al. | 356/36 |
| 4,007,301 | 2/1977 | DeMartino | 210/778 X |
| 4,008,736 | 2/1977 | Wittmann-Liebold et al. | 137/606 |
| 4,065,412 | 12/1977 | Dreyer | 422/129 X |
| 4,168,724 | 9/1979 | Graffunder et al. | 251/61.1 X |
| 4,252,769 | 2/1981 | Hood et al. | 422/81 X |
| 4,284,241 | 8/1981 | Azalbert | 239/524 X |

FOREIGN PATENT DOCUMENTS

| | | | |
|---|---|---|---|
| 2241513 | 3/1973 | Fed. Rep. of Germany | 436/89 |
| 257124 | 11/1969 | U.S.S.R. | 436/89 |

OTHER PUBLICATIONS

A Device Coupled to a Modified Sequenator for the Automated Conversion of Anilinothiazolinones into PTH Amino Acids, Wittmann-Liebold et al; Analytical Biochemistry, 75,621–633, 1976.

Aminopropyl Glass and its p-Phenylene Diisothiocyanate Derivative, a New Support in Solid-Phase Edman Degradation of Peptides and Proteins, Wachter et al; FEBS Letters, vol. 35, No. 1, 9/73.

Direct Microsequence Analysis of Polypeptides Using an Improved Sequenator a Nonprotein(Polybrene), and High Pressure Liquid Chromatography Hunkapiller et al; American Chemical Soc. Vol. 17, No. 11, '78, 2124–2133.

Primary Examiner—Michael S. Marcus
Assistant Examiner—Michael S. Gzybowski
Attorney, Agent, or Firm—Joseph E. Mueth

[57] ABSTRACT

An improved apparatus and method for the sequential performance of chemical processes on a sample of chemical material wherein the sample is embedded in a solid matrix of fluid permeable material located within a reaction chamber and is sequentially subjected to a plurality of fluids passed through the chamber in a pressurized stream, causing chemical interaction between the sample and the fluids.

28 Claims, 27 Drawing Figures

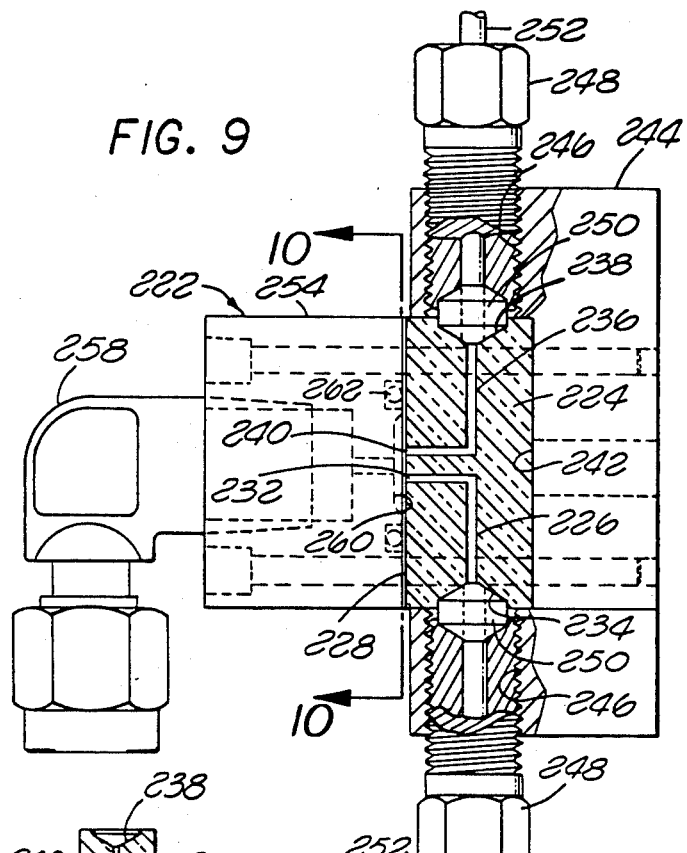
FIG. 9
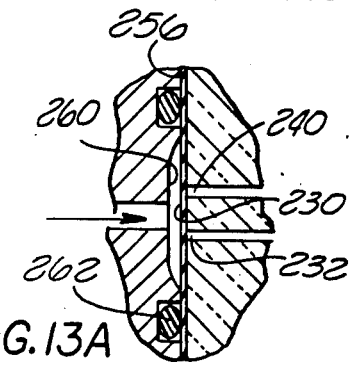
FIG. 10
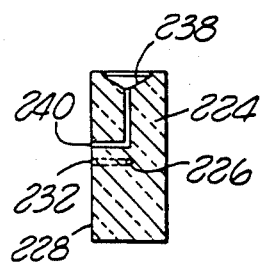
FIG. 12A
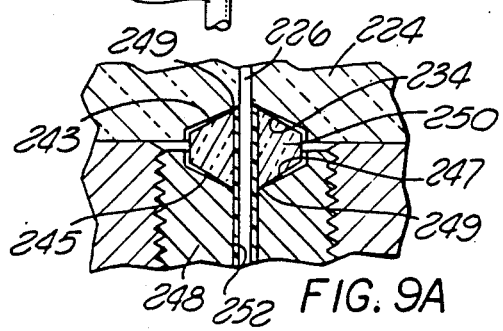
FIG. 9A
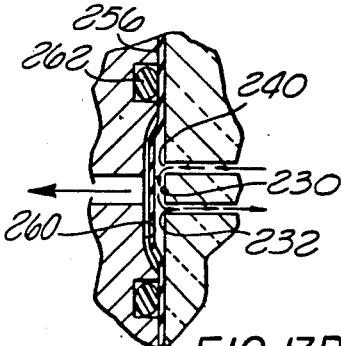
FIG. 13A
FIG. 13B
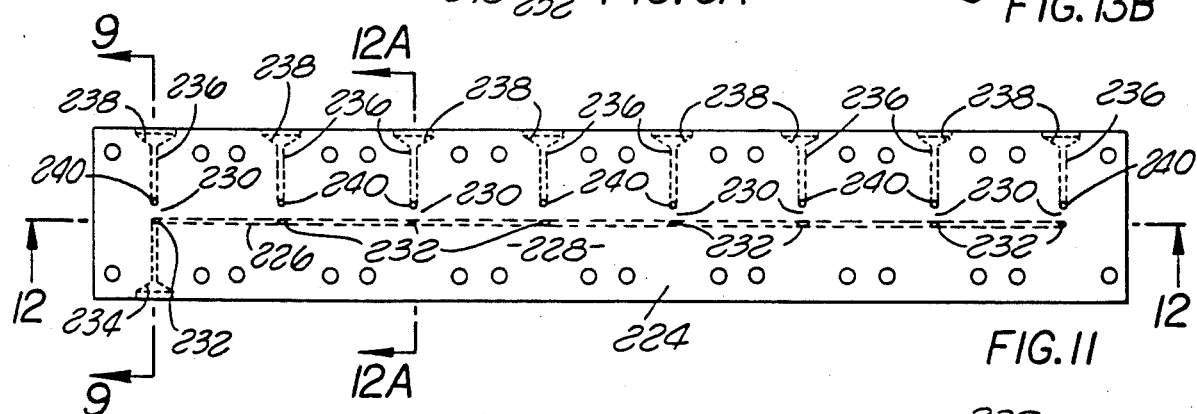
FIG. 11
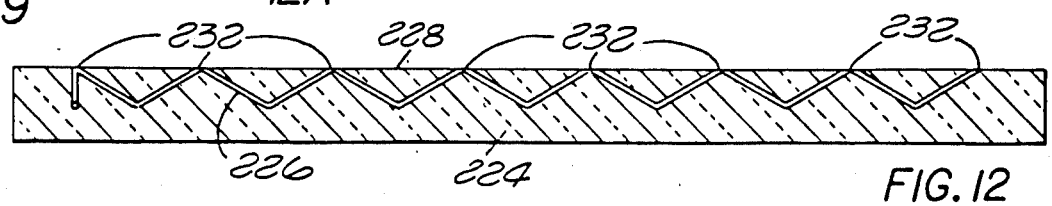
FIG. 12

TABLE 1

| | | Step | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 |
|---|---|---|---|---|---|---|---|---|---|---|---|---|---|---|---|---|---|---|---|---|---|---|---|---|---|---|---|---|---|---|---|
| | | Time (sec) | 2 | 2 | 4 | 7 | 10 | 40 | 4 | 300 | 20 | 80 | 2 | 10 | 7 | 46 | 30 | 20 | 60 | 60 | 2 | 90 | 2 | 4 | 4 | 2 | 60 | 4 | 450 | 20 | 30 |
| FRAC. COLL. | VACUUM | | | | | | | | | | | | | | | | | | | | | | | | | | | | | | |
| | WASTE | | | X | X | X | X | X | X | X | X | X | X | X | X | X | X | X | X | X | X | X | X | X | X | X | X | X | X | X | X |
| | ARGON | | | X | X | X | X | X | X | X | X | X | X | X | X | X | X | X | X | X | X | X | X | X | X | X | X | X | X | X | X |
| FLASK | WASTE 2 | | | | | | | | | | | | | | | | | | | | | | | | | | | | | | |
| | COLLECT | | | | | | | | | | | | | | | | | | | | | | | | | | | | | | |
| | DELIVER/ARGON | | X | | X | | | | | | | | | | | | | | | | | | | | | | | | | | |
| | VACUUM | | | | | | | | | | | | | | | | | | | | | | | | | | | | | | |
| | WASTE 1 | | | | X | X | | | | | | | | | | | | | | | | | | | | | | | | | |
| | ARGON | | X | X | | | | | | | | | | | | | | | | | | | | | | | | | | | |
| | S4 | | | | | | | | | | | | | | | | | | | | | | | | | | | | | | |
| | R4A | | | | | | | | | | | | | | | | | | | | | | | | | | | | | | |
| | R4 | | | | X | X | | | | | | | | | | | | | | | | | | | | | | | | | |
| REACTION CHAMBER | VACUUM | | | | X | X | X | | | | | X | | | | | X | | | X | | | | X | | | | X | | | X |
| | COLLECT | | | | | | | | | | | | | | | | | | | | | | | | | | | | | | |
| | WASTE | | | | | | | X | | | | | | X | | | X | | | | | X | | | X | | | | X | | |
| | DELIVER | | | | | | | | | | | | | | | | | | | | | | | | | | | | | | |
| | ARGON | | | X | | | X | | | | | X | | | | | X | | | | X | | | | X | | | X | | | |
| | S3 | | | | | | | | | X | | | | | | | | | | | | | | | | | | | | | |
| | S2 | | | | | | | | | | | | | | | | | | | | | | | | | | | | | | |
| | S1 | | | | | | | | | | | | | | | | | | | | | | | | | | | | | | |
| | R3A | | | | | | | | | | | | | | | | | | | | | | | | | | | | | | |
| | R3 | | | | | | | | X | | | | | | | | | | | | | | | | | | | | | | |
| | R2 | | | | | | | | | | | | | | | | | | | | | | | | | | | X | | | |
| | R1 | | | | | | | | | | | | | | | | | | | | | | | X | | | | | | | |
| | CONVERSION FLASK OPERATIONS | | DELAY | PRESSURIZE | R4 ARGON LINE FLUSH | R4 DELIVER | LINE FLUSH | CONVERSION | " | " | " | " | " | " | " | " | " | " | " | " | " | " | " | " | " | " | " | " | " | " | " |
| | REACTION CHAMBER OPERATIONS | | DELAY | PRESSURIZE | VACUUM | VACUUM | VACUUM | VACUUM | R3 ARGON, PRESSURIZE | R3 DELIVER | LINE FLUSH | VACUUM | PRESSURIZE | S3 ARGON, LINE FLUSH | S3 DELIVER | S3 PRECIPITATION | S3 DELIVER | LINE FLUSH | VACUUM FLUSH | VACUUM | PRESSURIZE | VACUUM | PRESSURIZE | R1 ARGON, LINE FLUSH | R1 DELIVER | LINE FLUSH | VACUUM FLUSH | R2 ARGON, PRESSURIZE | R2 DELIVER | LINE FLUSH | VACUUM FLUSH |

| | | 30 | 30 | | CONVERSION |
|---|---|---|---|---|---|
| | | 31 | 2 | | " |
| | | 32 | 2 | | PRESSURIZE |
| | ⊠ | 33 | 4 | | R1 ARGON, LINE FLUSH |
| | | 34 | 2 | | R1 DELIVER |
| | | 35 | 2 | | LINE FLUSH |
| | | 36 | 60 | | VACUUM FLUSH |
| | | 37 | 4 | | R2 ARGON, PRESSURIZE |
| | | 38 | 450 | | R2 DELIVER |
| | | 39 | 40 | | LINE FLUSH |
| | | 40 | 60 | | VACUUM FLUSH |
| | | 41 | 2 | | PRESSURIZE |
| | | 42 | 60 | | VACUUM |
| | | 43 | 2 | | PRESSURIZE |
| | | 44 | 90 | | VACUUM |
| | | 45 | 2 | | DELAY |
| | | 46 | 2 | | PRESSURIZE |
| | | 47 | 10 | | S1 ARGON, LINE FLUSH |
| | | 48 | 3 | | S1 DELIVER |
| | | 49 | 40 | | S1 PRECIPITATION |
| | | 50 | 60 | | S1 DELIVER |
| | | 51 | 10 | | S2 ARGON, LINE FLUSH |
| | | 52 | 90 | | S2 DELIVER |
| | | 53 | 20 | | LINE FLUSH |
| | | 54 | 60 | | VACUUM FLUSH |
| | | 55 | 2 | | PRESSURIZE |
| | | 56 | 60 | | VACUUM |
| | | 57 | 2 | | PRESSURIZE |
| | | 58 | 90 | | VACUUM |
| | | 59 | 60 | | PRESSURIZE |
| | | 60 | 2 | | DELAY |

| | | |
|---|---|---|
| R3 ARGON, LINE FLUSH | VACUUM FLUSH | 61 | 4 |
| R3 DELIVER | VACUUM FLUSH | 62 | 190 |
| R3 DELIVER | VACUUM | 63 | 20 |
| R3 DELIVER | PRESSURIZE | 64 | 2 |
| R3 DELIVER | VACUUM | 65 | 20 |
| LINE FLUSH | PRESSURIZE | 66 | 10 |
| LINE FLUSH | S4 ARGON, LINE FLUSH | 67 | 10 |
| VACUUM | S4 DELIVER | 68 | 9 |
| VACUUM | LINE FLUSH | 69 | 5 |
| VACUUM | FLASK FLUSH | 70 | 5 |
| VACUUM | COLLECT | 71 | 15 |
| VACUUM | S4 DELIVER | 72 | 2 |
| VACUUM | LINE FLUSH | 73 | 5 |
| VACUUM | FLASK FLUSH | 74 | 5 |
| VACUUM | COLLECT | 75 | 35 |
| VACUUM | COLLECTOR STEP | 76 | 1 |
| PRESSURIZE | VACUUM | 77 | 2 |
| LINE FLUSH | VACUUM | 78 | 60 |
| S3 ARGON, LINE FLUSH | PRESSURIZE | 79 | 4 |
| S3 DELIVER | LINE FLUSH | 80 | 7 |
| S3 PRECIPITATION | LINE FLUSH | 81 | 46 |
| S3 DELIVER, COLLECT | LINE FLUSH | 82 | 15 |
| S3 SOAK | LINE FLUSH | 83 | 60 |
| S3 DELIVER, COLLECT | LINE FLUSH | 84 | 14 |
| S3 SOAK | LINE FLUSH | 85 | 50 |
| LINE FLUSH, COLLECT | LINE FLUSH | 86 | 20 |
| VACUUM FLUSH | LINE FLUSH | 87 | 60 |
| VACUUM | LINE FLUSH | 88 | 60 |
| PRESSURIZE | LINE FLUSH | 89 | 2 |
| VACUUM | VACUUM | 90 | 90 |
| DELAY | VACUUM | 91 | 60 |
| JUMP TO STEP 1 | JUMP TO STEP 1 | 92 | 0 |

4,704,256

APPARATUS FOR THE SEQUENTIAL PERFORMANCE OF CHEMICAL PROCESSES

This application is a continuation of application Ser. No. 190,100, filed Sept. 23, 1980, now abandoned.

BACKGROUND OF THE INVENTION

This invention relates generally to an improved apparatus and method for the performance of chemical processes and, more particularly, to an improved apparatus for automaticlly performing the sequential degradation of protein or peptide chains containing a large number of amino acid units for purposes of determining the sequence of those units.

The linear sequence of the amino acid units in proteins and peptides is of considerable interest as an aid to understanding their biological functions and ultimately synthesizing compounds performing the same functions. Although a variety of techniques have been used to determine the linear order of amino acids, probably the most successful is known as the Edman Process. Various forms of the Edman Process and apparatuses for automatically performing the processes are described in the following publications:

Edman and Begg, "A Protein Sequenator," European J. Biochem. 1 (1967) 80-91; Wittman-Liebold, "Amino Acid Sequence Studies of Ten Ribosomal Proteins of Escherichia coli with an Improved Sequenator Equipped with an Automatic Conversion Device," HoppeSeyler's Z. Physiol. Chem. 354, 1415 (1973); Wittman-Liebold et al., "A Device Coupled to a Modified Sequenator for the Automated Conversion of Anilinothiazolinones into PTH Amino Acids," Analytical Biochemistry 75, 621 (1976); U.S. Pat. No. 3,959,307 issued to Wittmann-Liebold and Graffunder on May 25, 1976, for "Method to Determine Automatically the Sequence of Amino Acids;" Hunkapiller and Hood, "Direct Microsequence Analysis of Polypeptides Using an Improved Sequenator, A Nonprotein Carrier (Polybrene), and High Pressure Liquid Chromatography," Biochemistry 2124 (1978); Laursen, R. A. Eur. J. Biochem. 20 (1971); Wachter, E., Machleidt, H., Hofner, H., and Otto, J., FEBS Lett. 35, 97 (1973); U.S. Pat. No. 3,725,010 issued to Penhasi on Apr. 3, 1973, for "Apparatus for Automatically Performing Chemical Processes;" U.S. Pat. No. 3,717,436 issued to Penhasi et al. on Feb. 20, 1973, for "Process for the Sequential Degradation of Peptide Chains;" U.S. Pat. No. 3,892,531 issued to Gilbert on July 1, 1975, for "Apparatus for Sequencing Peptides and Proteins;" U.S. Pat. No. 4,065,412 issued to Dreyer on Dec. 27, 1977, for "Peptide or Protein Sequencing Method and Apparatus." A further apparatus of note is described in copending U.S. patent application Ser. No. 106,828 filed Dec. 26, 1979 by Leroy E. Hood and Michael W. Hunkapiller, two of the applicants hereon, on "Apparatus for the Performance of Chemical Processes."

Briefly, as discussed in the above publications, the Edman sequential degradation processes involve three stages: coupling, cleavage and conversion. In the coupling stage phenylisothiocyanate reacts with the N-terminal α amino group of the peptide to form the phenylthiocarbamyl derivative. In the cleavage step anhydrous acid is used to cleave the phenylthiocarbamyl derivative to form the anilinothiazolinone. After extraction of the thiazolinone the residual peptide is ready for the next cycle of coupling and cleavage reactions. Aqueous acid is used to convert the thiazolinone to the phenylthiohydantoin which may be analyzed in an appropriate manner, such as by chromatography.

The automated apparatus of the Penhasi U.S. Pat. No. 3,725,010, as modified in the above-referenced articles of Wittmann-Liebold and the pending patent application Ser. No. 106,828 of Hunkapiller and Hood, relates to an automated sequenator in which the reactions are carried on in a thin film formed on the inside wall of a rotating reaction cell which is commonly known as a "spinning cup" and is located within a closed reaction chamber. Means are provided for introducing and removing controlled amounts of liquid reagents relative to the chamber for reaction with a sample of a protein or peptide in an inert atmosphere. The sample to be analyzed is initially placed in the spinning cup, followed by the sequential introduction and withdrawal of the various reagents and solvents necessary for carrying out the coupling and cleavage reactions. The liquid reagents and solvents themselves form films on the walls of the cup which pass over and interact with the sample film as the cup spins. The reagents dissolve the sample film and perform the coupling and cleavage stages of the Edman process. Upon completion of the coupling and cleavage stages, the reaction chamber is evacuated to remove volatile components of the reagents. Following the post-coupling evacuation, the remaining sample film is extracted with solvent to remove non-volatile components. Following the post-cleavage evacuation, the resulting thiazolinone is extracted from the sample film with solvent and transferred either to a separate flask for conducting the conversion step or to an apparatus for collection and drying of the various fractions. In cases where the conversion process is not performed immediately in a conversion flask, the process may be performed later on a number of fractions simultaneously.

The introduction and withdrawal of fluids relative to the spinning cup has been achieved with fluid conduits passing through a plug which seals an opening in the upper wall of the reaction chamber and depends therefrom to a location within the cup. Fluids are introduced directly into the spinning cup at a point adjacent the bottom thereof, and are withdrawn from an annular groove in the cylindrical interior surface of the cup. The fluid to be withdrawn is forced into the annular groove by centrifugal force when the cup is rotated at a high rate, and is withdrawn through a conduit having an inner end projecting into the groove. This effluent conduit thus acts as a scoop for removing the reaction products and by-products and the extracting solvents.

If the protein or peptide sample in a spinning cup device does not have sufficient mass to form a cohesive film by itself, it is sometimes carried on the inner wall of the cup during the solvent extractions within a relatively thick layer of nonprotein carrier material. The carrier material and the sample are then dissolved in the liquid reagents during the reaction stages to enable the coupling and cleavage reactions to take place. A polymeric quaternary ammonium salt having the chemical composition 1,5-dimethyl-1,5-diazaundecamethylene polymethobromide has been used for this purpose. The carrier must be applied in substantial quantities to securely retain the sample, and the carrier and sample are both dissolved by the liquid reagents to permit reaction between the sample and the reagents.

Although devices of the spinning cup type can provide acceptable experimental results in many cases, they have several disadvantages. For example, the expenses of obtaining a suitably large protein or peptide sample and maintaining an adequate supply of the necessary reagents are quite high, primarily because the reagents used are in liquid form and must be used in substantial quantities. Liquid reagents and solvents tend to separate portions of the sample from the film and wash them from the wall of the cup as they pass, reducing the yield of terminal amino acid units obtained in each successive cycle of the apparatus. The initial quantity of sample must therefore be great enough to insure that sufficient sample will remain through the last cycle to produce useful results. Devices of this type also have rather long cycle times due to the considerable volume of the reaction chamber and the need to repeatedly remove semi-volatile liquid reagents and solvents by vacuum drying the sample therein. In addition, spinning cup sequenators are quite complex and expensive, both to manufacture and repair.

A different type of sequencing device is disclosed in the above-cited Laursen and Wachter papers, wherein the sample is immobilized by covalent linkage to the surfaces of a plurality of small beads. The beads form a porous packing within a reaction column, and the column is flooded with liquid reagents to perform the chemical processes. Because the cleavage reagents used are excellent solvents for proteins and peptides, the covalent linkage must be complete in order to hold the sample in place. However, covalent linkage is difficult to obtain in practice. The packed column is also difficult to wash, and the beads therein tend to disintegrate during use.

There have heretofore been proposed sequencing devices designed to overcome the deficiencies of these apparatuses by containing a sample within a stationary reaction chamber and subjecting the sample to at least one reagent in gas or vapor form. The Gilbert and Dreyer patents cited above disclose two such devices, neither of which operates entirely satisfactorily.

The device of the Gilbert patent provides a closed finger-shaped extension within a reaction chamber for holding a peptide or protein sample at a controlled temperature during sequential exposure to gaseous reagents and solvents. Each time a reagent is introduced, the extension is cooled internally to produce condensation thereon. The extension is then warmed, causing the sample to dissolve in the liquid, and the reaction proceeds. After reacting with the sample, the unwanted semi-volatile chemicals may either be dried from the sample by a combination of heat and a stream of inert gas, or be washed from the extension along with the terminal amino acid by a solvent which is condensed on the extension until it drips therefrom.

In the device and method of the Dreyer patent, a protein or peptide sample is applied to both the inner and outer surfaces of many small macroporous beads within a reaction column by chemical coupling or direct adsorption thereto. Various reagents and solvents are passed sequentially through the packed column in either gaseous or liquid form to produce the desired degradation reactions. The flow of reagents and solvents to the column is controlled by a ten position rotary face seal valve.

Unfortunately, the devices of the Gilbert and Dreyer patents do not provide a sufficiently contamination-free environment to achieve acceptable results through a large number of degradation cycles. For example, it is difficult to efficiently wash the protein or peptide sample in the Gilbert and Dreyer devices. The Gilbert method of washing the sample by condensation of solvent thereon to the point at which solvent drips from the sample would tend to leave traces of the various reaction products on the sample, contaminating future chemical reactions. Likewise, the packing used to retain the sample within the reaction column of Dreyer is difficult to wash because the various chemical products must be transported entirely through it and away from the column to avoid contamination. This is not easily done even when large amounts of solvent are used, because the solvent tends to pass through the spaces between the beads rather than through the small pores inside the beads where most of the protein sample is located. The fluid feed lines and flow valves of the Gilbert and Dreyer devices are also difficult to fully evacuate and are prone to trapping chemical residues which can interfere with the intended chemistry of further reaction cycles.

The glass or plastic beads used as packing in the reaction column of Dreyer also have a tendency to disintegrate over a number of degradation cycles, clogging the system to the point at which the passage of fluids therethrough is hindered. It then becomes virtually impossible to wash the system between cycles and the chemistry within the column becomes hopelessly contaminated.

The contamination caused by the several factors described above has a cumulative effect over the duration of a sequential degradation process. The sample and the reagents within the reaction cell thus become more and more contaminated, hindering the desired coupling and cleavage reactions and causing a number of undesired reactions to take place. The yield from each complete cycle of the apparatus is thus decreased and a series of contaminants is introduced into the fractions.

The yield is further decreased by direct loss of the sample due to a variety of reasons, including the disintegration of the packing, solubility of the sample in the flushing solvents, and failure of the sorptive bonds between packing and sample.

While these effects may be overlooked in some cases where large amounts of the protein or peptide sample are available or where the chain has a relatively small number of units, they become devastating in cases where the chain has a very large number of units or only very small amounts of the particular protein or peptide are available. Both of these circumstances are present in the case of interferon, a small protein made in human cells in response to certain viral infections. Interferon has recently caused a great deal of excitement in the world of clinical medicine because it promises to be an effective agent for arresting viral infections and it appears to offer considerable hope as an anti-cancer reagent. Interferon is produced and, accordingly, is available only in very small quantities. Currently, virtually the entire world's production of the two types of human interferon originates in the relatively few world centers that have access to large quantities of human white blood cells (leukocyte interferon) or certain human cells in tissue culture (fibroblast interferon). Because of this limited productive capacity of interferon, it has been difficult to carry out well controlled clinical studies and fundamental analyses of how this molecule functions. To further complicate the picture, interferon is composed of a chain of approximately 150 amino acid units, which must be individually cleaved from the chain for analysis. Contamination losses of the types described above can prevent the sequencing of any but the first few amino acid units of interferon with the very small quantities of the protein available. Beyond the first few cleavage cycles, the small sample can become contaminated to the point at which positive results are unobtainable.

The most sophisticated prior device known to the applicants herein for converting the various thiazolinones cleaved from the sample into the more stable phenylthiohydantoins is the conversion flask described in the above-referenced articles of Wittmann-Liebold, as modified in the co-pending patent application Ser. No. 106,828 of Hunkapiller and Hood. However, applicants have found that this flask suffers from inefficient washing of its inner walls when reagents and solvents are introduced through the appropriate capillary tube. It has been suggested that the reagents and solvents can be delivered with a stream of inert gas to wash the flask walls by splattering the liquid thereon, however, this technique causes an erratic flow of liquid to the flask and makes it very difficult to control the volume of liquid delivered.

Applicants have also found that when the prior conversion flask is scaled down appreciably in size to accommodate lower volumes of liquid, it is difficult to obtain the optimum degree of dispersion of inert gas bubbles within the liquid contents of the flask to agitate the contents during the conversion reaction and evaporate the semi-volatile components thereof. Inert gas introduced to the bottom of the flask for these purposes tends to rise to the surface of the liquid in relatively large bubbles which do not uniformly agitate the liquid and instead promote splattering of the liquid onto the top of the flask.

Therefore, in many applications it is desirable to provide an apparatus for performing chemical processes such as the sequencing of proteins or peptides which operates efficiently and with a minimum of system contamination to enable the maximum number of sequencing cycles to be successfully performed with a very small amount of sample.

SUMMARY OF THE INVENTION

Briefly, the present invention comprises chamber means having an interior surface defining a reaction chamber, the chamber having inlet and outlet means for conduction of fluids therethrough in a pressurized stream, and solid matrix means permeable by diffusion to a plurality of fluids and located within the chamber, such that a sample embedded in the matrix means is immobilized and exposed to any of a plurality of fluids passed through the chamber for chemical interaction therewith.

The chamber means may include surface means supporting the solid matrix means as a thin film thereon, and the matrix means may comprise a polymeric quaternary ammonium salt such as 1,5-dimethyl-1,5-diazaundecamethylene polymethobromide or poly(N,N-dimethyl-3,5-dimethylene piperidinium chloride).

The surface means may comprise all or a portion of the interior wall of the chamber means, or may comprise porous sheet means extending substantially tranversely across the chamber and permitting passage of the fluids therethrough. The sheet means may comprise a sheet made of a plurality of glass fibers.

The chamber means may comprise a pair of abutting chamber elements having first and second cavities, respectively, on opposed mating surfaces thereof, the first and second cavities being aligned with each other to form the reaction chamber. The first and second cavities may be tapered in directions away from the mating surfaces to locations at which they communicate with the inlet and outlet means, respectively. The porous sheet means, if used, is received within a recess in at least one of the mating surfaces for retention within the chamber in an orientation substantially separating the first and second cavities. The chamber means may include at least one sheet of yielding material sandwiched between the mating surfaces in a sealing relationship, the yielding material being permeable to the plurality of fluids. At least one of the chamber elements may then include a raised portion on a mating surface thereof which extends about the cavity therein to compress the sheet of yielding material against the mating surface of the chamber element and thus enhance the sealing relationship.

The inlet and outlet means may comprise a pair of capillary passages extending through the chamber elements, respectively, and communicating at inner ends thereof with the reaction chamber on opposite sides of the porous sheet means. The capillaries may be coaxial with the reaction chamber and extend therefrom to outer capillary openings at substantially flat outer surfaces of the chamber elements.

The means for sequentially passing a plurality of fluids through the chamber may comprise valve block means having a plurality of substantially flat valving sites on the surface thereof, the valve block means defining a primary passage continuous between two ends thereof and communicating through primary openings with each of the valving sites, and a plurality of secondary passages each communicating through a secondary opening with one of the valving sites; and a plurality of resilient, substantially impermeable diaphragms covering the respective valving sites, each of the diaphragms being actuable between a first sealing condition in which it is forced against one of the valving sites to close off the primary and secondary openings communicating with that site and a second condition in which it is drawn away from the site to provide a fluid flow path between the primary and secondary openings over the exterior of the valve block means; whereby fluid flow between the primary passage and the secondary passage can be selectively controlled. The connecting means may comprise at least one tapered ferrule closely received in sliding engagement over a tubing member and urged against a differently tapered recess in the valve block means communicating with one of the passages therein, such that an inward force applied to said ferrule is focused on a relatively small area of contact between the ferrule and the recess to produce a fluid seal therebetween. The recess is preferably tapered at a greater angle than said ferrule. The connecting means may further include a fitting at one end of the primary passage for connecting the primary passage to another portion of the apparatus such that the primary passage serves as a manifold which can be flushed by a flow of fluid between the fitting and the secondary passage furthest away from the fitting. The primary passage may comprise a plurality of straight passages connected end to end to form a conduit having a sawtooth configuration and communicating at alternating intersections thereof with the respective valving sites.

The apparatus may include a conversion flask having a plurality of capillary tubes extending into the interior thereof for the introduction and withdrawal of various fluids, at least one of the capillary tubes having an inner end at which the bore is closed and which is provided with a plurality of restricted radially-spaced orifices, such that passage of fluids through the capillary tube produces a spray onto the interior walls of the flask to wash them down. A capillary tube terminating at a point adjacent the bottom of the flask may also have a closed end with a plurality of restricted radially-spaced orifices adjacent thereto, such that passage of a gas inwardly through the capillary tube produces a plurality of small bubbles agitating any liquid within the flask and accelerating the drying thereof.

The method of the present invention for sequentially performing chemical processes on a sample of chemical material comprises embedding the sample in a solid matrix which is permeable by diffusion to a plurality of fluids, enclosing the solid matrix within a closed chamber having an inlet and an outlet, and sequentially passing the plurality of fluids through the chamber as a pressurized stream from the inlet to the outlet thereof such that the sample is exposed to each of the fluids, whereby the sample is immobilized and chemical interaction between the sample and the fluids is obtained. The solid matrix may be supported as a thin film on the inner walls of the closed chamber. Alternatively, the solid matrix may be supported on a porous sheet which extends substantially transversely across the chamber at a location between the inlet and outlet such that fluid passed from the inlet to the outlet must pass through the sheet. The step of embedding the sample in a solid matrix may comprise the steps of applying the solid matrix to a support surface as a thin film and then applying a solution containing the sample to the film such that the sample solution dissolves the matrix. The liquids are then evaporated from the solution, leaving behind a film with the sample embedded therein.

It is an object of the present invention to provide an apparatus and method for the sequential performance of chemical processes on a sample of chemical material with a minimum of sample loss and a minimum of system contamination.

It is also an object of the present invention to provide an economic apparatus and method for the sequential performance of chemical processes on a sample of very small size through the use of minimum amounts of reagents and solvents.

It is another object of the present invention to provide an improved apparatus and method for the sequential performance of chemical processes having a very short cycle time.

It is a still further object of the present invention to provide an improved apparatus and method for the sequential performance of chemical processes on a sample wherein the sample is more effectively washed between cycles.

The apparatus and method of the present invention solves a number of the problems of the prior sequenators by immobilizing the protein or peptide sample within a solid matrix formed as a thin film permeable by diffusion to both the reagents and solvents used in the degradation process. The difficult problem of attaining complete covalent linkage is thus avoided, as is the problem of sample loss experienced when the sample is directly adsorbed onto a support surface and fully exposed to the mechanical shearing forces of the mobile liquid phase. The sample is securely held in place by the matrix, while the smaller reagents, solvents and amino acid derivatives are able to diffuse through the matrix, in effect dissolving in the matrix to a sufficient concentration to carry on the various steps in the degradation process. The solid matrix retains the sample so effectively when exposed to gaseous reagents that virtually any shape of sample support surface can be used without causing sample loss. The inner walls of the reaction chamber itself may be a sufficient support surface.

A support surface which greatly facilitates complete washing of the system is a porous sheet made of a plurality of overlapping glass fibers and extending transversely across a flow-through reaction chamber. The porosity is provided by spaces between the fibers. This structure possesses a relatively high total surface area with a minimum dimension in the direction of fluid flow. The solid matrix forms a thin film on the surfaces of the fibers, enabling reagents and solvents to readily diffuse into the film to interact with the sample embedded therein. This enables chemical processes and wash cycles to be performed on the sample with a minimum of reagents and solvents and in a relatively short period of time. The reagents and solvents, some of which are in the form of a gas or vapor, permeate the thin film to contact the sample and interact therewith as completely and efficiently as possible.

The relatively thin profile of the porous sheet disclosed herein further enhances the ability of the sample to be thoroughly washed of residual reagents and reaction products with a relatively small amount of solvent. The solvent need only move the reagents and reaction products the relatively short distance beyond the surface of the sheet to remove them from the system. From a point outside the surface of the sheet they may be easily conducted out of the chamber to leave the sample in condition for the next reaction step. The low solvent usage not only represents a savings in the cost of solvent, but also reduces the tendency of the sample to be washed from the reaction chamber and lost.

The use of reagents in gas or vapor form also contributes to complete exposure of the sample to the reagents, minimizing the amount of reagents required. Low reagent usage is important because the reagents used in the Edman degradation technique must be extremely free of contamination and therefore are very expensive. Further, the sample and the solid matrix containing it are not dissolved by the gaseous reagents, eliminating the problem of sample loss due to separation of the sample from the support surface.

The reaction chamber of the present invention is constructed to allow passage of both gaseous and liquid reagents through the porous sheet holding the sample without allowing the sample to become contaminated with external impurities or with chemicals carried over from one reaction step or cycle to another. The abutting chamber elements thus combine to form a low volume reaction chamber made up of first and second cavities on opposite sides of the porous sheet. A pair of capillary passages extending oppositely through the respective chamber elements from the chamber itself enable a plurality of fluids in gas or liquid form to be passed as a pressurized stream through the chamber and past the sample matrix. The low volume of the chamber and the passages minimizes the volumes of reagents and solvents required, and facilitates vacuum drying of the system between cycles. The two chamber elements are sealed at mating surfaces thereof against a sheet of yielding material sandwiched between the mating surfaces. The yielding material is permeable to the plurality of fluids passed through the chamber, and in fact, improves the flow of gases through the chamber by disbursing the gases to more uniformly contact the porous sheet.

An alternative embodiment of the reaction chamber is a single capillary tube or capillary-type passage having a solid matrix formed as a thin film on the interior surface or bore thereof. The protein or peptide sample is embedded in the matrix, as in the case of the porous sheet, and the reagents and solvents are passed sequentially through the tube to interact with the sample. The chamber structure described above can be used for this purpose without the porous sheet element. The sample-containing matrix is then formed on the surfaces of the first and second cavities. Similarly, the surface supporting the solid matrix can be constructed in virtually any way which enables the reagent and solvent fluids to be passed over the matrix.

The novel valve assemblies of the present invention for controlling the flow of fluids to and from both the chamber and the conversion flask are especially constructed to eliminate cross-contamination of the fluids. Each of the valve means interfaces a single conduit with a plurality of other conduits for selectively connecting the single conduit to each of the others. The single conduit is made to communicate with one end of the primary passage in the valve block while each of the other conduits is connected to one of the secondary passages. In the normal closed condition, each of the diaphragms covering the various valving sites is forced by gas pressure against the surface of the valve block to prevent communication of the primary passage with the secondary passage leading to the particular valve site. Fluid communication between the single conduit and the other conduits may be selectively provided by applying vacuum to one or more of the diaphragms to draw the diaphragms away from the valving sites and allow fluid to pass over the surface of the valve block lying between the openings to the respective passages. The secondary passage leading to the valving site at the remote end of the primary passage may be connected to a pressurized source of a flushing fluid, such as inert gas, for the purpose of completing the delivery of each fluid through the valve. Thus, after a particular reagent or solvent is introduced into the reaction chamber by applying a vacuum to the corresponding diaphragm of the delivery valve, the diaphragm at the remote end of the primary passage may be opened to complete the delivery by forcing any of the reagent or solvent remaining within the primary passage to the chamber. This is possible due to the continuity of the primary passage, and results in the manifold formed thereby being purged of a particular reagent or solvent before delivery of the next reagent or solvent is commenced. In the case of the valve at the outlet to the reaction chamber, the primary passage is connected to the outlet while the secondary passages are connected to the conversion flask, vacuum and waste, respectively. The continuity of the primary passage enables it to be thoroughly evacuated and virtually eliminates the possibility that semi-volatile substances will be trapped therein between cycles.

It will be understood that the "sawtooth" configuration of the primary valve passages disclosed herein has previously been used in valve assemblies of others in the sequenator field. However, the prior sawtooth valve assemblies of which applicants are aware have incorporated a plurality of individual blocks mounted against valving sites on a main valve block to slide back and forth between conditions of communication and non-communication of passages within the main block. The sliding blocks tend to wear, causing leaks both to the atmosphere and between the passages. The novel valve assemblies disclosed herein solve the problem of wear by combining the prior sawtooth manifold with a series of diaphragms for establishing and cutting off flow between pairs of openings communicating with the respective passages. The diaphragms can be made of substantially inert materials, such as commercially available fluorocarbon polymers, which will function indefinitely without deterioration. Moreover, the prior means for connecting the valve passages to external conduits tend to produce excessive pressure on the sides of the valve block, promoting distortion of the upper sealing surface of the valve block and loss of its ability to form a seal. In particular, the prior sawtooth valves of which applicants are aware connect external conduits to the valve passages by pressing substantially flat flange surfaces associated with the various conduits against the sides of the valving block to produce a series of seals between pairs of flat surfaces. Because each of these components is made of materials such as fluorocarbon polymers which are very difficult to accurately machine, a considerable amount of pressure must be applied to conform the respective sealing surfaces to each other and form the required seal. The pressure is borne by the valve block, causing distortion of its upper sealing surface.

The valve assemblies of the present invention incorporate a plurality of tapered ferrules receivable partially within differently tapered recesses in the valve block to effect a seal without the application of undue pressure to the valve block. A relatively small sealing force is focused on a particular portion on the ferrule to seal the ferrule against the corresponding tapered recess without distorting the block.

The provision of interfaces at opposite ends of the ferrules between surfaces having different tapers further enhances the seals obtained. Interfaces of this type between differently tapered surfaces are preferably provided on opposite sides of the ferrules to obtain optimum sealing characteristics.

The conversion flask of the present invention enables reagents and solvents to be introduced in the form of a spray impinging on the interior walls of the flask to wash any chemicals which may have been condensed or splattered thereon down the walls and into the body of liquid within the flask. A major source of cross-contamination of the system between cycles is thus eliminated. The conversion flask also enables gases to be passed upwardly through the body of liquid in the form of small bubbles which uniformly agitate the liquid and aid in drying semi-volatile components thereof, without causing sample loss due to excessively vigorous bubbling and splattering. This promotes rapid, gentle removal of liquid from the sensitive amino acid derivatives. Solvent used to carry the amino acid derivatives into the conversion flask can thus be removed in a much shorter time than in the Wittmann-Liebold patent cited above (1 to 2 minutes rather than 5 to 10 minutes) and at a lower temperature (40° to 50° C. rather than 50° to 80° C.). This significantly improves yields of the most unstable amino acid derivatives, such as those of serine, threonine, histidine, arginine, and tryptophan. Reagents used in the conversion flask can be removed by a combination of fine streams of inert gas bubbles and low vacuum in 3 to 5 minutes rather than the 30 to 40 minutes required under the Wittmann-Liebold patent. In the process of the Wittmann-Liebold patent, drying of the reagent must commence immediately upon its introduction to the amino acid residue in the conversion flask in order to meet the requirement that the total conversion flask cycle time be no greater than the total cycle time of the primary reaction chamber. Since the acid component of the conversion reagent, trifluoroacetic or hydrochloric acid, is much more volatile than the water in which it is dissolved, the acid component tends to be removed early in the drying process of Wittmann-Liebold leaving the amino acid derivative in nothing but a water solution for a significant portion of the conversion stage. This causes incomplete conversion of the derivatives of glycine and proline and decomposition of other derivatives. In the present conversion apparatus, the conversion reagent can be left in contact with the amino acid derivatives for a time sufficient for complete conversion, 30 to 40 minutes, and then dried rapidly, in 3 to 5 minutes, without splattering the sample throughout the interior of the conversion flask.

BRIEF DESCRIPTION OF THE DRAWINGS

The above and other objects of the present invention may be more fully understood from the following detailed description taken together with the accompanying drawings wherein similar reference characters refer to similar elements throughout and in which;

FIG. 9 is a vertical cross-sectional view of a diaphragm valve assembly constructed in accordance with the present invention for controlling the flow of fluids to and from the reaction chamber and the conversion flask, taken in a direction corresponding to the line 9—9 in FIG. 11;

FIG. 9A is a fragmentary enlarged cross-sectional view of one of the connector elements of the valve assembly illustrated in FIG. 9;

FIG. 10 is a vertical cross-sectional view taken along the line 10—10 of FIG. 9;

FIG. 11 is a side elevational view of the manifold block of the valve apparatus illustrated in FIG. 9;

FIG. 12 is a horizontal cross-sectional view taken along the line 12—12 of FIG. 11;

FIG. 12A is a vertical cross-sectional view taken along the line 12A—12A of FIG. 11;

FIG. 13A is an enlarged fragmentary cross-sectional view of the valving portion of the valve assembly of FIG. 9, showing the diaphragm pressed against the manifold block to prevent fluid communication between the passages at that location;

FIG. 13B is an enlarged fragmentary cross-sectional view of the valving portion of the assembly of FIG. 9, showing the diaphragm drawn away from the manifold block to permit fluid flow between the passages;

DESCRIPTION OF THE PREFERRED EMBODIMENTS

Figure 1:
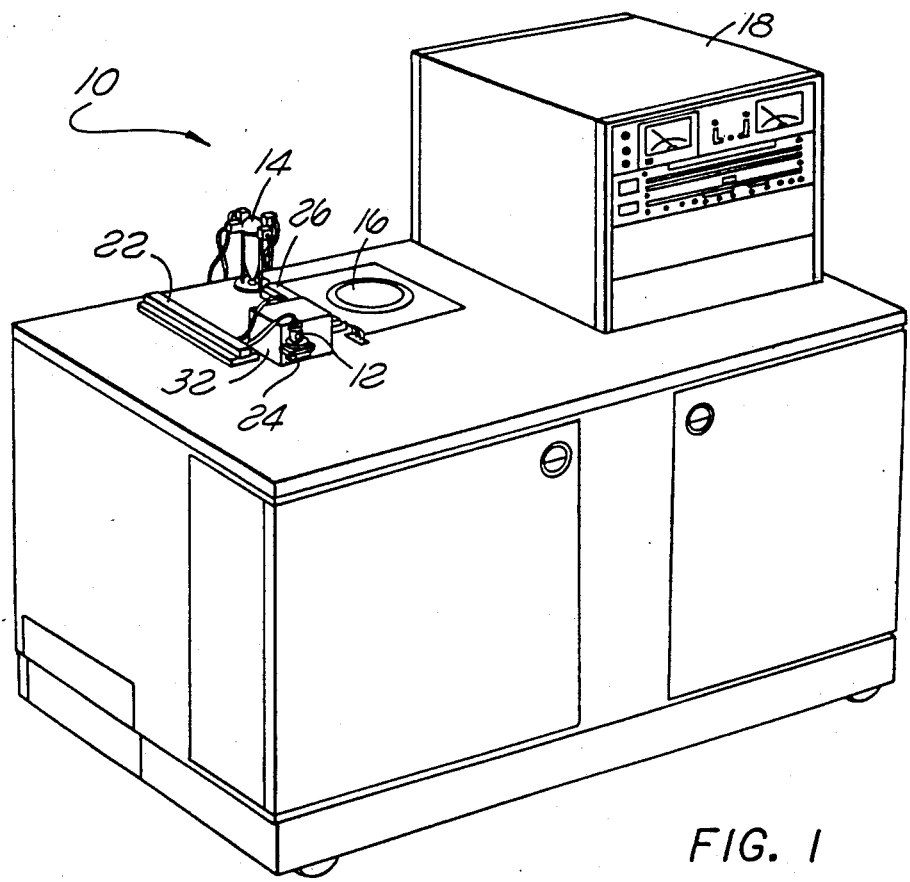
FIG. 1 is a perspective view of an apparatus constructed in accordance with the present invention.
Figure 2:
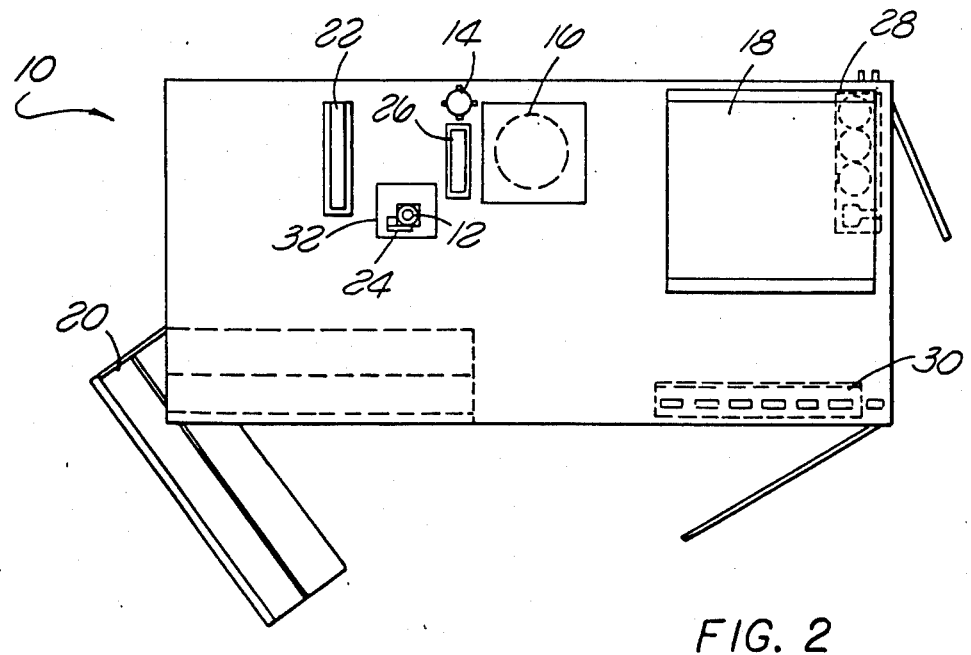
FIG. 2 is a top plan view of the apparatus of FIG. 1.

Referring now to the drawings there is illustrated, in FIGS. 1 and 2 thereof, an apparatus embodying the present invention, generally designated 10. The apparatus 10 includes a chamber apparatus 12, a conversion flask 14 and a fraction collector 16, each of which is operated through an automatic control unit 18. An array 20 of pressurized solvent and reagent reservoirs are connected through a bank 22 of diaphragm-type flow valves to the reaction chamber 12 and the conversion flask 14. A second bank of valves 24 regulates the flow of liquids from the reaction chamber to the conversion flask 14 and other locations. A third bank of diaphragm valves 26 serves to connect the conversion flask and fraction collector to either waste or vaccum, and to regulate fluid flow from the flask to the fraction collector.

A filtered inert gas source 28 supplies the apparatus 10 with highly purified inert gas, preferably argon, for pressurizing the solvent and reagent reservoirs, purging oxygen-bearing air from the system and accelerating the process of drying out the reagents and solvents within the system at various times. A bank 30 of pressure-regulating valves and gauges serves to individually regulate the pressure of the gas to each solvent and each reagent reservoir, and to each of the other components of the apparatus 10.

Figure 3:
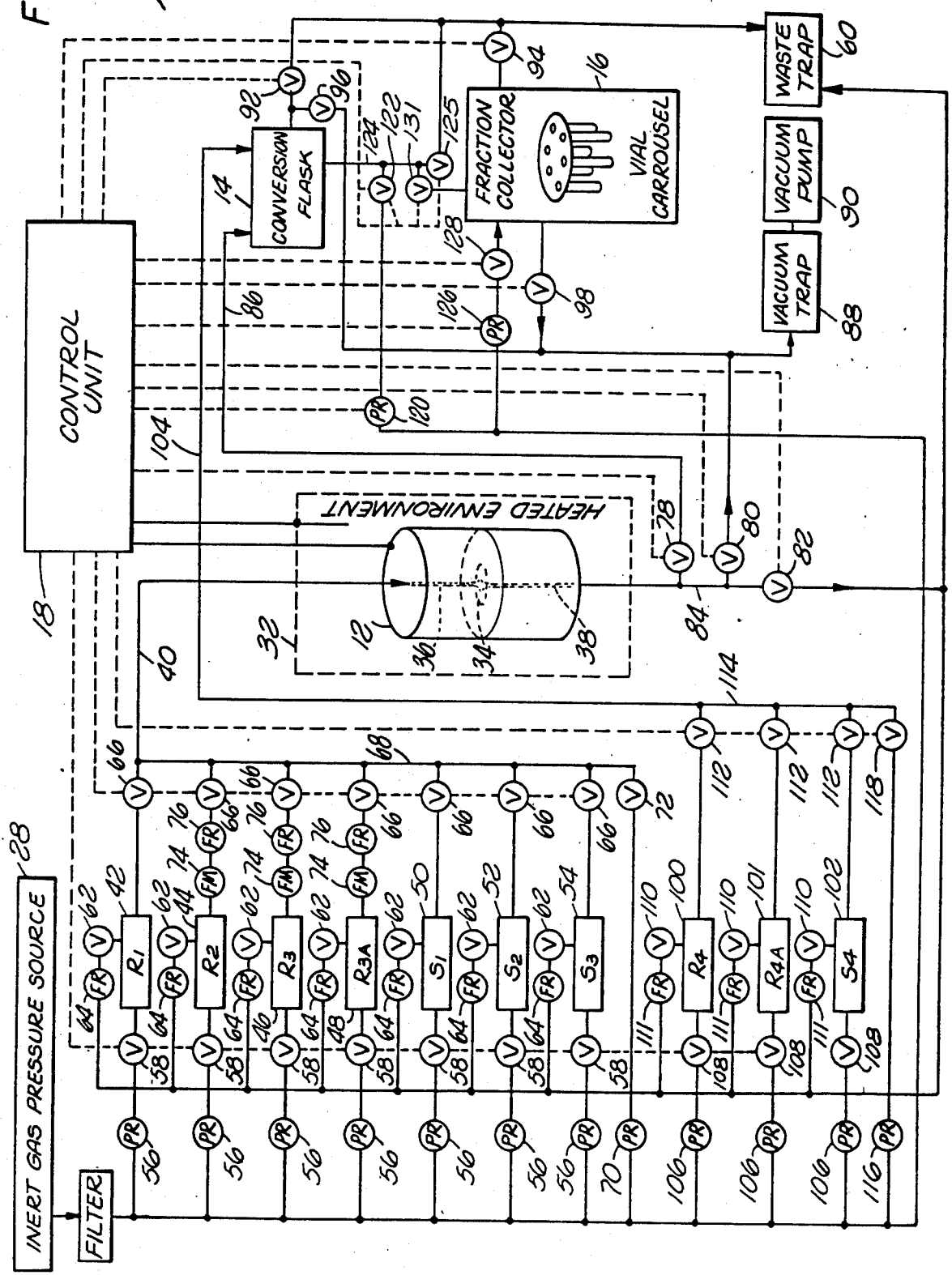
FIG. 3 is a schematic diagram of the apparatus of FIG. 1.

The operation of the apparatus 10 is depicted in FIG. 3. The chamber apparatus 12 is located within a heated environment 32 and, in the preferred embodiment, defines a reaction chamber 34 communicating with inlet and outlet passages 36 and 38, respectively. The inlet passage 36 is connectible through a fluid conduit 40 to a plurality of reservoirs of the array 20, namely, reagent reservoirs 42, 44, 46 and 48, and solvent reservoirs 50, 52 and 54. The reservoirs 42 through 54 are pressurized by the inert gas pressure source 28 through an array of individual gas pressure regulators 56 and solenoid flow valves 58. Each of the reservoirs 42 through 54 is also connectible at a point above the fluid level therein to a waste trap 60 through an individual flow valve 62 and an individual flow regulator 64. Pressurized inert gas introduced to the reservoirs from the source 28 can thus be vented to the waste trap 60 at a rate controlled by the flow regulators 64. The fluid outputs of the reservoirs 42 through 54 are individually controlled through diaphragm valves 66 communicating with a continuous manifold 68 which is connected at one end to the fluid conduit 40. Fluid from the pressurized reservoirs 42 through 54 can thus be passed through the conduit 40 and the chamber inlet passage 36 to the reaction chamber 34 by the selective actuation of the valves 66. To aid in the delivery of the reagents and solvents and to flush the manifold 68 and conduit 40 after delivery, pressurized inert gas from the source 28 may be introduced to the manifold 68 at the end opposite to the conduit 40 through a pressure regulator 70 and a diaphragm valve 72. Actuation of the valve 72 thus introduces pressurized gas at the remote end of the manifold 68, driving any reagents or solvents therein through the conduit 40 and the passage 36 to the reaction chamber 34.

The fluid outlets of the reservoirs 44, 46 and 48 are provided with gas flow meters 74 in series with flow regulators 76 because the reagents stored therein are used in gas or vapor form, while the remaining solvents and reagents are used in liquid form. The meters 74 and flow regulators 76 are necessary to accurately control the rate of gas discharge through the corresponding valves 66.

Fluid flow from the reaction chamber 34 is controlled by diaphragm valves 78, 80 and 82, which communicate with the outlet passage 38 through a continuous manifold 84. The valve 78 is opened to pass the desired product of reaction, typically the N-terminal amino acid unit of a protein or peptide sample, through the conduit 86 to the conversion flask 14. The valve 82 may be opened to connect the outlet passage 38 to the waste trap 60 for disposal of unwanted reagents, solvents and reaction products, and the valve 80 connects the outlet passage 38 to a vacuum trap 88 and a vacuum pump 90 for evacuation of the reaction chamber 34, the outlet passage 38 and the manifold 84.

Similarly, the conversion flask 14 and the fraction collector 16 are connectible to the waste trap 60 through valves 92 and 94, respectively, and to vacuum through the valves 96 and 98.

Reagent reservoirs 100 and 101 and a solvent reservoir 102 are provided to supply reagents and solvent to the conversion flask 14 through a conduit 104. The reservoirs 100, 101 and 102 are pressurized by the inert gas source 28 through pressure regulators 106 and solenoid valves 108, and are connected to the waste trap 60 through individual vent valves 110 and flow regulators 111. The fluid outlets of the reservoirs 100, 101 and 102 are connected through diaphragm valves 112 to a continuous manifold 114 which communicates at one end with the conduit 104. The flow of fluid from the pressurized reservoirs may thus be produced by selectively opening the valves 112 to expel either reagent or solvent into the manifold 114. The source of inert gas is connectible through a pressure regulator 116 and a diaphragm valve 118 to the end of the manifold 114 opposite the conduit 104 to propel the reagent or solvent through the manifold and the conduit to the conversion flask 14.

The inert gas pressure source 28 is also connected to the conversion flask through a pressure regulator 120, a diaphragm valve 122 and a conduit 124, and to the fraction collector 16 through a pressure regulator 126 and a valve 128. When a particular fraction has been converted to the intended manner within the flask 14, it can be expelled from the flask by gas pressure through the conduit 124 and a valve 131 to the fraction collector 16 for storage within a vail therein. After the fraction is expelled, the flask 14 can be filled to a relatively high level with solvent to dissolve any residual chemicals therein. The solvent can then be expelled by gas pressure through the conduit 124 and a valve 125 to the waste trap 60, flushing the flask in preparation for delivery of the next amino acid derivative.

The fraction collector 16 comprises basically a carrousel of vials actuated by the control unit 18 once during each cycle of the apparatus 10 to place an empty vial in position to receive the next succeeding fraction of amino acid units from the flask 14.

The control unit 18 is preferably a fully automated unit controlling the diaphragm valves 66, 72, 78, 80, 82, 92, 94, 96, 98, 112, 118, 122, 125, 128 and 131, as well as the solenoid valves 58, 62, 108 and 110. The control unit 18 also controls the mechanism for maintaining the heated environment 32 at the desired temperature (not shown), the fraction collector 16, the vacuum pump 90, and a variety of sensors throughout the system. The various gas pressure regulators and flow regulators described above are manually adjusted upon set-up to establish the desired pressures and flows within the corresponding fluid conduits.

Figure 4:
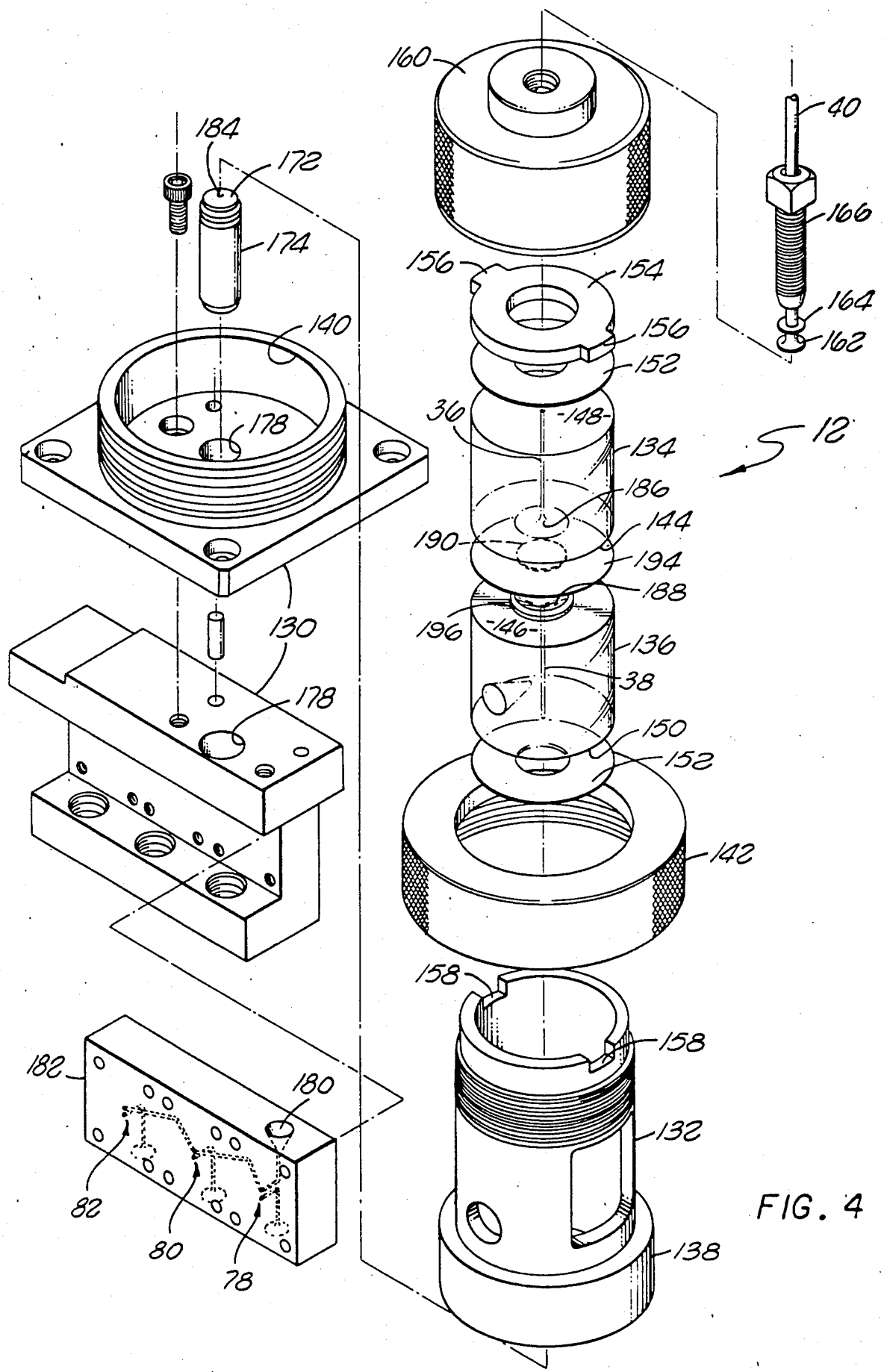
FIG. 4 is an enlarged exploded perspective view of a reaction chamber assembly constructed in accordance with the present invention.
Figure 5:
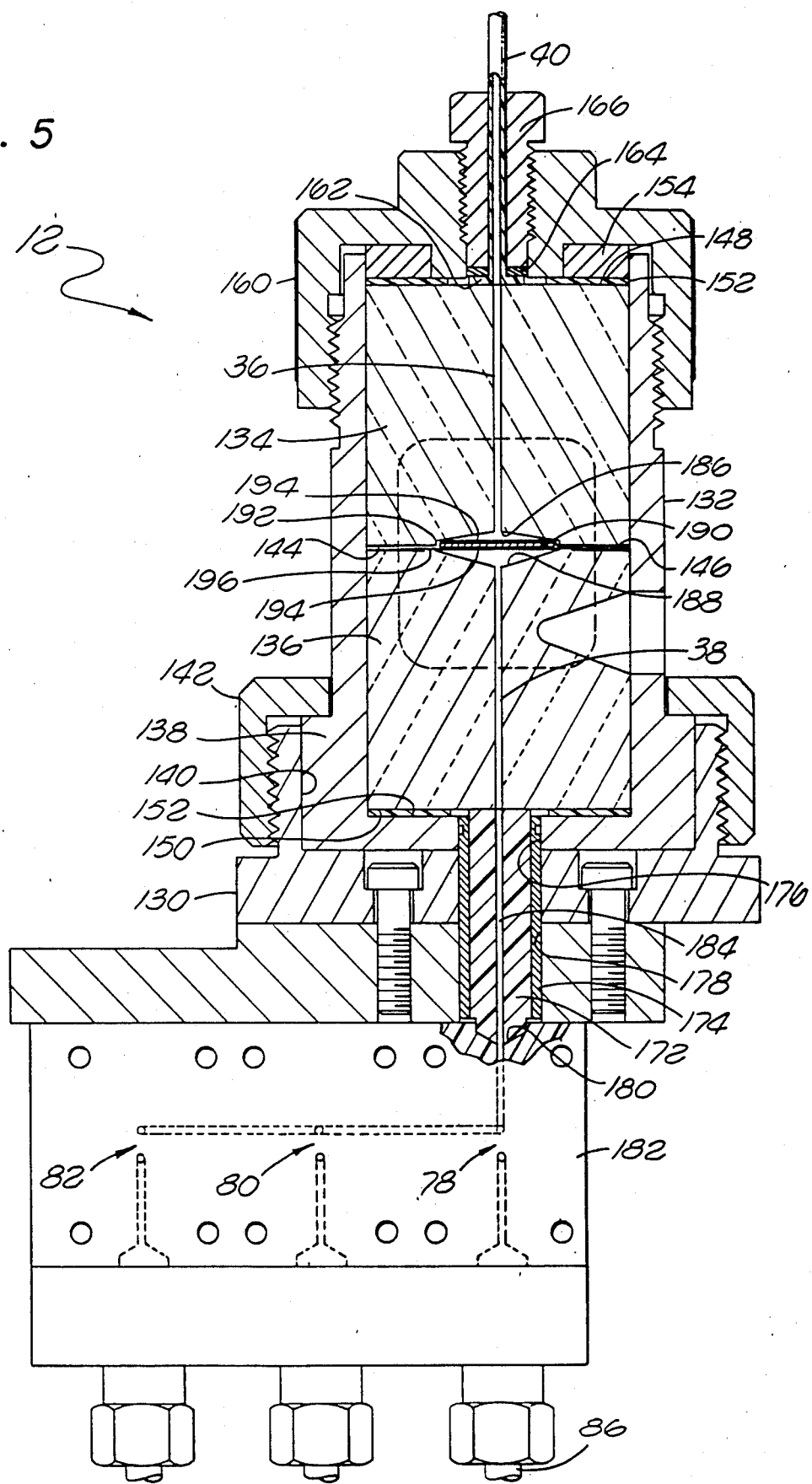
FIG. 5 is an enlarged vertical cross-sectional view taken along the line 5—5 of FIG. 4.

The chamber apparatus 12 is shown in detail in FIGS. 4 and 5 to comprise a two-piece base 130 supporting a sleeve 132 which contains first and second chamber elements 134 and 136, respectively. The sleeve 132 is provided with an enlarged cylindrical portion 138 centered about the axis of the sleeve and closely received within a cylindrical recess 140 of the base 130. The cylindrical portion 138 is held in position by a retaining collar 142 which is threadingly engaged with the base 130.

The chamber elements 134 and 136 are cylindrical glass elements having opposed mating faces 144 and 146, respectively, and closely received in axial alignment within the sleeve 132. The inlet and outlet passages 36 and 38, described above, extend axially through the chamber elements 134 and 136, respectively, and are preferably capillary passages having a diameter on the order of 1 millimeter. The axially outer ends 148 and 150 of chamber elements 134 and 136, respectively, are generally flat and are abutted with a pair of thin resilient washers made of a substantially inert material to provide the chamber elements with a cushion in the axial direction relative to the sleeve 132. A metallic washer 154 located on top of the upper resilient washer 152 is provided with opposed locking ears 156 for engaging slots 158 in the upper end of the sleeve 132. The metallic washer 154 is held in position by a cap 160 threaded to the upper end of the sleeve 132 to snugly hold the chamber elements in place relative to the sleeve. The engagement of the ears 156 with the slots 158 prevents the washer 154 from rotating when the cap 160 is installed, thus preventing the cap from damaging the assembly by rotating the chamber elements. The fluid conduit 40 is provided with a flared lower end 162 which abuts the outer end 148 of the chamber element 134 such that the bore of the conduit 40 communicates with the inlet passage 36. The conduit 40 carries a backup washer 164 and a fitting member 166 which is threaded axially into the cap 160 to force the flared end 162 against the chamber element 134 in a sealing relationship. The conduit 40 may be made of any resilient substantially inert material, such as commercial fluorocarbon polymers. The alignment of the bore of the conduit 40 with the inlet passage 36 is assured by precision construction of the various interfitting components about a common axis.

The outlet passage 38 is placed in communication with the continuous manifold 84 described above by a mass 172 of substantially inert material encased within a steel sleeve 174. The sleeve 174 has a smooth exterior received within aligned axial openings 176 and 178 of the enlarged cylindrical portion 138 and the base 130, respectively. The mass 172 extends axially in either direction beyond the steel sleeve 174 to engage the outer end 150 of the second chamber element 136 and a tapered recess 180 of a valve block 182 which defines the manifold 84. An axial passage 184 within the mass 172 is precisely aligned with the outlet passage 38 and one end of the manifold 84 to provide a single continuous capillary passageway from the chamber element 136 to the valve block 182. As in the case of the conduit 40 discussed above, the accurate construction of the related components about a common axis insures precise alignment and complete sealing between the various passages. The chamber apparatus 12 can thus be easily disassembled and reassembled in a very short time without compromising alignment of the various passages or the integrity of the various seals.

The valve block 182 is of a novel construction which will be described in detail in relation to FIGS. 9 through 13. It will suffice to note at this point that portions of the valves 78, 80 and 82 are included within the valve block 182 to control the flow of fluid from the chamber apparatus 12.

Figure 6A:
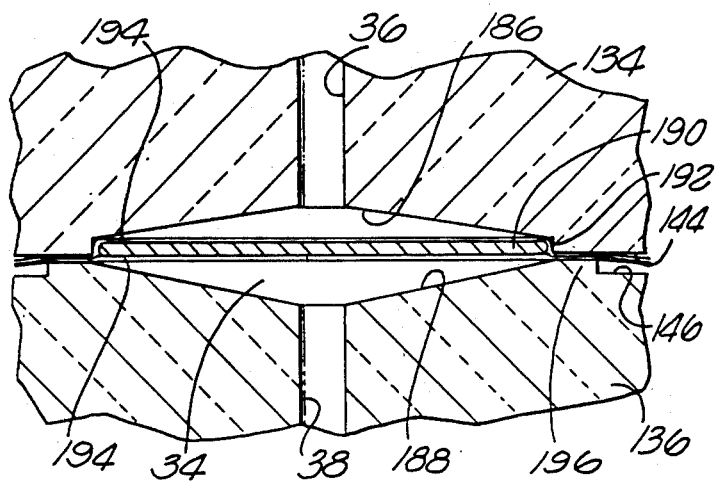
FIG. 6A is a further enlarged cross-sectional view of the reaction chamber illustrated in FIG. 5.

As seen most clearly in FIG. 6A, the chamber 34 is formed by aligned cavities 186 and 188 in the opposed mating surfaces 144 and 146, respectively, of the two chamber elements. The two cavities are arranged coaxially with the inlet and outlet passages 36 and 38 and are preferably circular in cross-section, providing an axially symmetric path for fluid passing from the inlet passage to the outlet passage. A porous sheet element 190 extends transversely across the reaction chamber 34 and may be received at least partially within a depression 192 of the cavity 186. The porous sheet element 190 thus separates the inlet passage 36 from the outlet passage 38 such that fluids flowing from one to the other must pass through the sheet element. The porous sheet element 190 preferably comprises a sheet or mat made of a compressed fibrous material, such as glass. Commercially available glass fiber filters are suitable for this purpose and have a high resistance to decomposition or other damage during use. It has been found that a porous sheet of this type provides a rather large surface for supporting a thin film in which a portion or peptide sample can be embedded. If the film is made of a fluid-permeable material, i.e. one which allows diffusion of liquids and gases into it, then the material can form a solid matrix which is able to securely hold the sample but permits chemical interaction of reagents and solvents with the sample. Polymeric quaternary ammonium salts, such as 1,5-dimethyl-1,5-diazaundecamethylene polymethobromide or poly(N,N-dimethyl-3,5-dimethylene piperidinium chloride), are ideal for this purpose. They permit diffusion of fluids, are insoluble in the solvents used and are chemically stable to both the reagents and solvents. In addition, they make a cohesive film and carry a positive charge which enables them to bond ionically to the glass support surface.

Figure 17A:
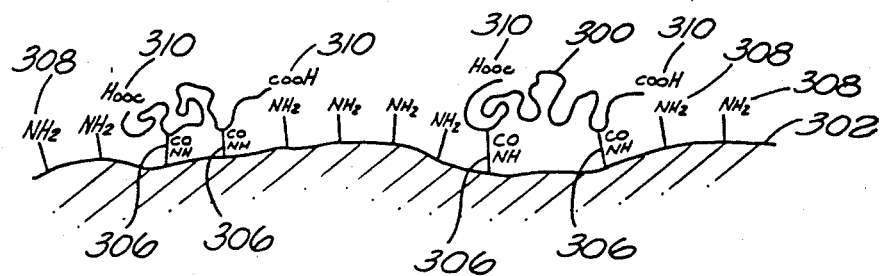
FIGS. 17A and 17B illustrate schematically the two primary prior art methods of immobilizing a protein or peptide sample during degradation.
Figure 17B:
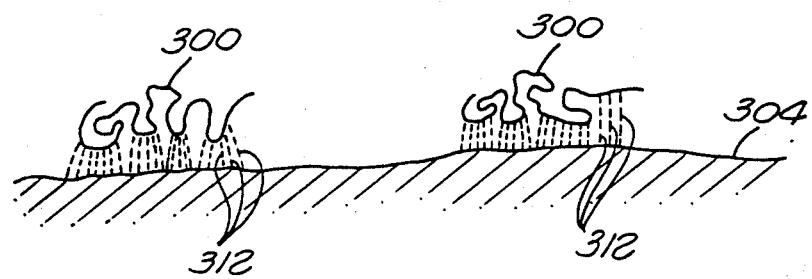
Figure 17C:
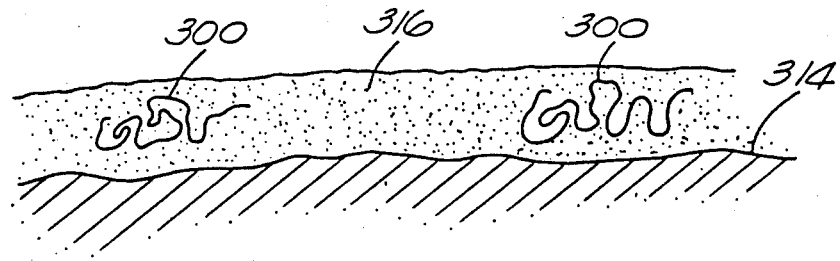
FIG. 17C illustrates schematically the immobilization of a protein or peptide according to the present invention.

The fundamental differences between the forms of sample retention practiced in the prior sequenators and that of the present invention will be understood most clearly in relation to FIGS. 17A, 17B and 17C. FIGS. 17A and 17B illustrate schematically the two most common prior methods of immobilizing a protein or peptide sample 300 relative to a sample support surface 302 or 304.

FIG. 17A illustrates the case in which the sample is chemically linked to a glass support surface 302 by covalent bonds 306. For example, the surface 302 may be specially treated such that some of the silica sites of the glass have functional amino groups 308 extending therefrom for reaction with carboxyl groups 310 on the sample chain. Under proper conditions some of the groups 308 and 310 will react, leaving the sample covalently bonded to the glass and releasing a number of water molecules. Bonds of this type are very strong, and one or two of them per molecule are sufficient to hold the sample in place. However, covalent bonding is difficult to achieve with protein and peptide samples. Also, covalent bonds hold the chain through a very few isolated units in the chain. When the degradation process reaches those units and cleaves them from the chain, the remainder of the chain is left unbound and can be washed from the chamber.

FIG. 17B illustrates the case in which the sample 300 is adsorbed directly onto a support surface 304. The sample is then held in place by a very large number of relatively weak noncovalent interactions 312 between the sample and the surface. On the molecular level, the surface interacts with many different sites on the sample. This works well in the case of large proteins and peptides, but as the sample gets sequenced down to a much smaller size it becomes susceptible to being knocked or drawn from the surface. This results in drastic sample loss.

FIG. 17C illustrates schematically the immobilization of the sample 300 relative to the support surface 314 by embedding it in a solid matrix 316 formed as a thin film thereon. As described above, the matrix 316 may be a polymeric quaternary ammonium salt which has a positive charge. The matrix will thus be firmly retained on an acidic glass surface by a very large number of ionic interactions, and will securely hold the sample in place because the sample is embedded in it. No reliance is placed in direct bonding interactions between the sample and the surface, and the effectiveness of the immobilization is not affected by diminishing sample size.

The present invention relies on diffusion of reagents, solvents and amino acid derivatives through the solid matrix 316 to effect chemical interaction with the embedded sample. The matrix is formed as a thin film which absorbs the reagents and solvents passed over it. Once dissolved in the film, the reagents and solvents are able to readily diffuse across its thickness to carry on the degradation process.

Returning now to FIG. 6A, the reaction chamber 34 is sealed at the periphery of the cavities 186 and 188 by at least one sheet 194 of a yielding sealing material sandwiched between the mating surfaces 144 and 146. A pair of yielding sheets 194 are preferably used, one on either side of the porous sheet element 190. The sheets 194 are very thin and are permeable to the plurality of reagent and solvent fluids to be passed through the chamber 34. An annular sealing ridge or bead 196 at the periphery of the cavity 188 bears against the sealing sheets 194 to provide a more effective seal against the surface 144 adjacent the periphery of the cavity 186. The sealing sheets 194 may be made of any substantially chemically inert material, such as a commercial fluorocarbon polymer, to minimize the possibility of seal deterioration. They serve not only to provide a seal for the chamber 34 but also to support the porous sheet element 190 and to diffuse gases and liquids passed through the chamber such that flow of the gases and liquids will be more evenly distributed across the element 190. Long system life and optimum chemical interaction with a sample are promoted in this way.

Figure 6B:
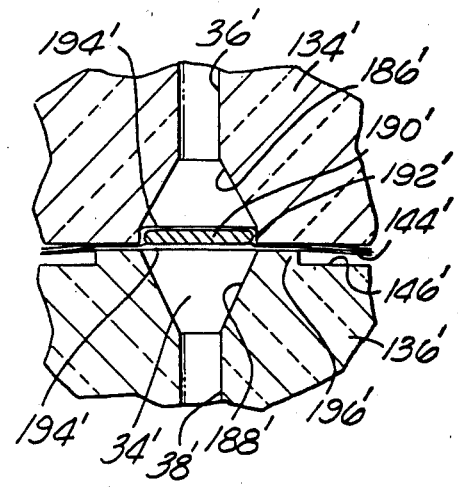
FIG. 6B is a cross-sectional view of a second embodiment of the reaction chamber illustrated in FIG. 5.

An alternative embodiment 34' of the reaction chamber of the present invention is illustrated in FIG. 6B, wherein the aligned cavities 186' and 188' in the opposed mating surfaces of the two chamber elements are somewhat narrower and longer than the cavities 186 and 188. Otherwise, the structures 34 and 34' are identical, and the various elements of the structure 34' in the drawings are numbered similarly to those of the structure 34 with the addition of "primes" (') to distinguish them. The reaction chamber 34' permits a somewhat more direct flow of fluids from the inlet 36' to the outlet 38', but restricts the diameter of the porous sheet element 190' therein.

Figure 6C:
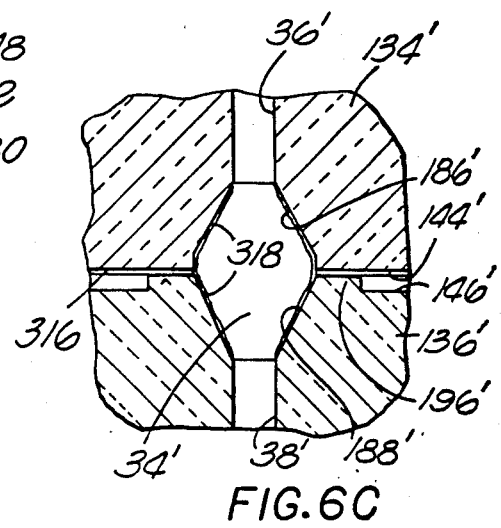
FIG. 6C is a cross-sectional view of the reaction chamber of FIG. 6B with the porous sheet element removed therefrom, for use with a sample-containing film applied to the interior surface thereof.

FIG. 6C illustrates the chamber 34' of FIG. 6B with the porous sheet element 190' remove therefrom. In addition, the sealing sheets 194' are replaced with a single annular sheet 316 of yielding material having a central opening equal to the diameter of the chamber. In this embodiment, a solid fluid permeable matrix 318 having a protein or peptide sample embedded therein is formed as a thin film on the walls of the chamber 34' for exposure to reagents and solvents passed through the chamber. The flow of fluids through the chamber 34' is thus enhanced, while a substantial film surface area is retained.

Figure 18A:
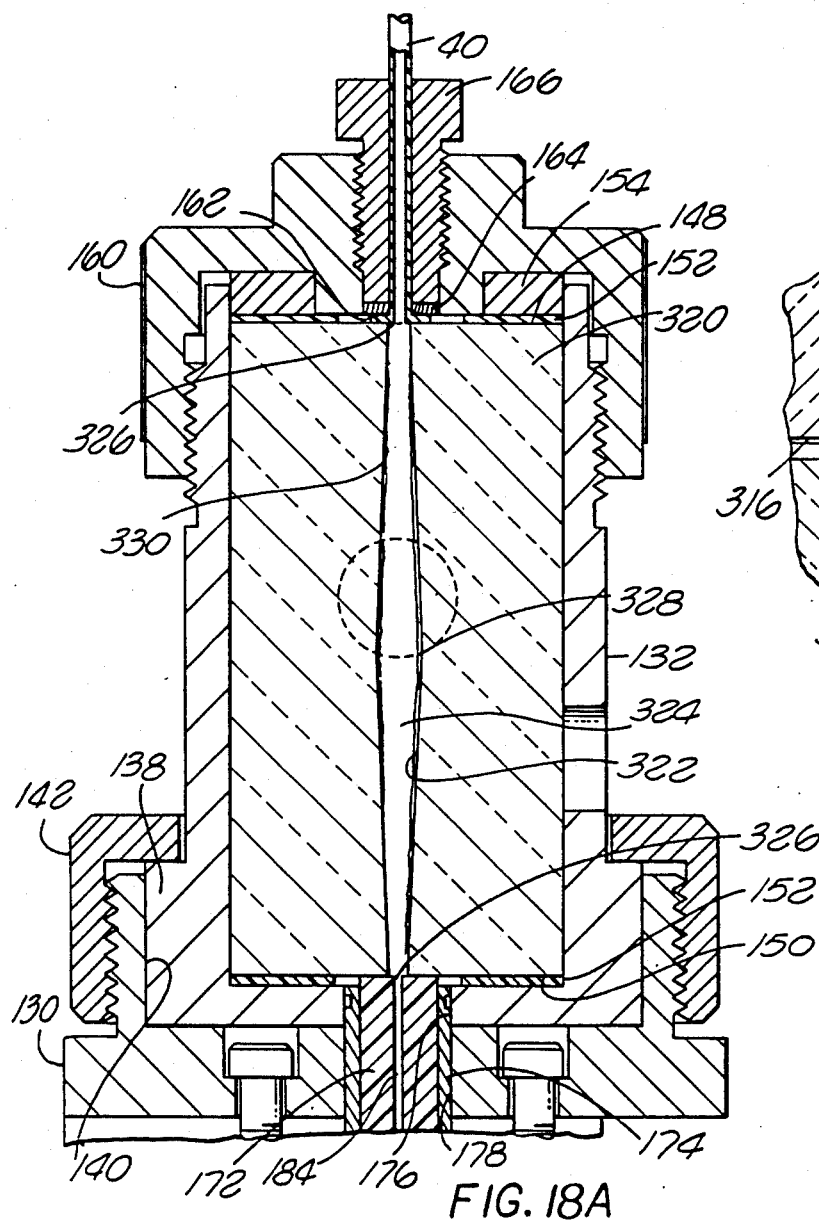
FIG. 18A is a fragmentary enlarged vertical cross-sectional view corresponding to FIG. 5, of a further embodiment of the reaction chamber assembly of the present invention.
Figure 18B:
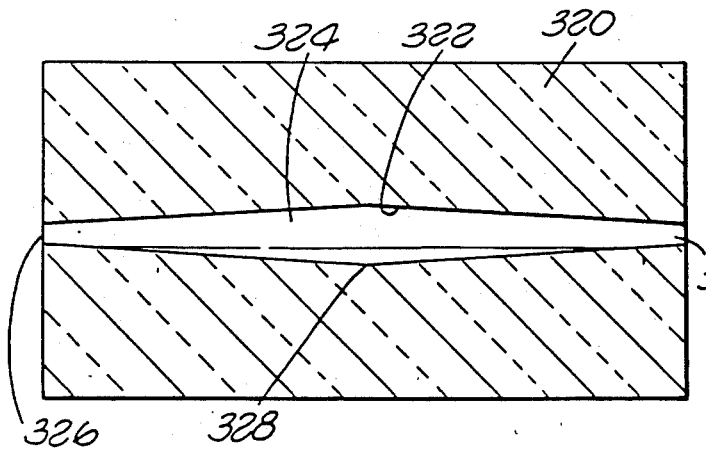
FIG. 18B is a vertical cross-sectional view showing the chamber element of the embodiment of FIG. 18A, turned on its side for the purpose of applying a sample-containing matrix to the interior walls thereof.
Figure 18C:
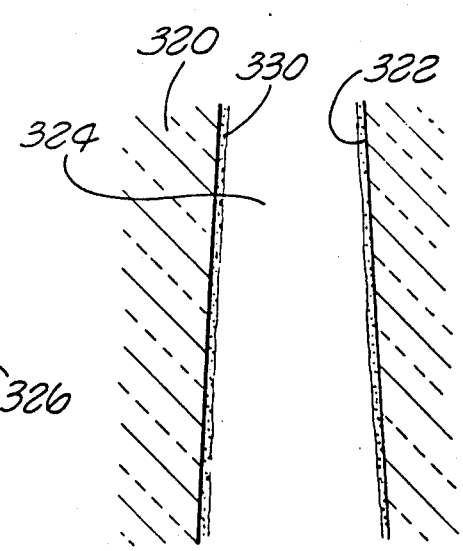
FIG. 18C is a further enlarged fragmentary cross-sectional view of the chamber element of FIG. 18B, with a sample-containing film applied to the interior walls thereof; and Table 1, as follows, is a listing of the various steps performed by the apparatus of the present invention in a typical degradation and conversion cycle.

A further embodiment of the chamber apparatus of the present invention is shown in FIGS. 18A, 18B and 18C, wherein the two chamber elements 134 and 136 are replaced by a single capillary-type chamber element 320 within the sleeve 132. The remaining elements of the chamber apparatus 12 are the same as those described in relation to FIGS. 4 and 5, and are numbered similarly. All structures and connections external to the chamber apparatus are also identical to those described above.

The chamber element 320 comprises a cylindrical glass structure having interior walls 322 defining an axial capillary-type chamber 324. The chamber 324 increases uniformly in diameter from its two ends 326 toward its middle 328, and the protein or peptide sample is carried within a solid matrix 330 formed as a thin film on the walls 322.

It will be understood that the reaction chamber of the present invention can take virtually any form having a sample support surface past which a plurality of reagent and solvent fluids can be passed. For example, a single elongated capillary tube (not shown) would suffice for the chamber apparatus 12, with a fluid-permeable solid matrix formed on the interior surface or bore thereof. Fluids passed through the tube would interact with a protein or peptide sample embedded in the film to perform the degradation process.

Figure 7:
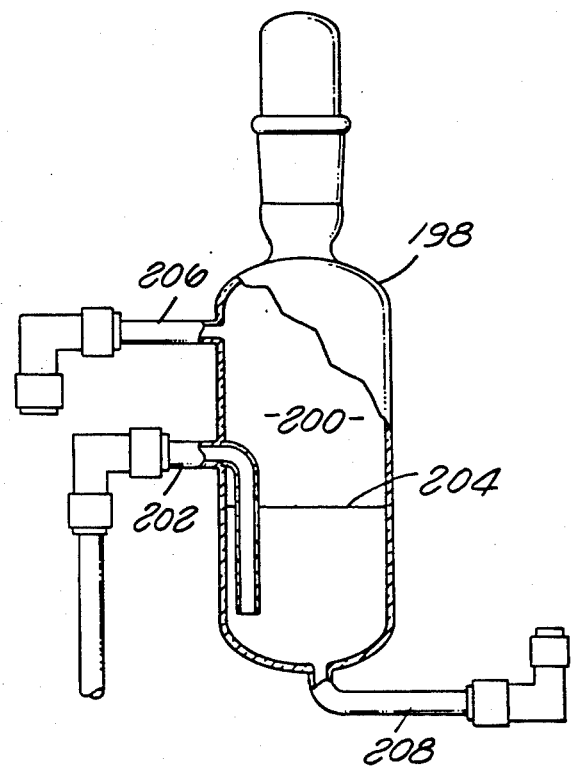
FIG. 7 is a vertical cross-sectional view of a typical reservoir of the present invention for a reagent or solvent to be used in liquid form.

A typical reservoir 198 of the present invention for storage and delivery of a liquid reagent to the reaction chamber 34, 34' or 324 is shown in FIG. 7. The reservoir 198 corresponds to the reservoirs 42, 50, 52, 54, 100, 101 and 102 of FIG. 3. A pressurized inert gas is supplied to the interior 200 of the reservoir 198 by a conduit 202 communicating therewith at a point below a level 204 of the liquid reagent or solvent therein. The pressurized gas thus introduced draws any dissolved oxygen from the liquid and can be released at a controlled rate through a vent conduit 206 to produce a dynamic equilibrium condition within the interior 200. A liquid outlet 208 is provided for the controlled expulsion of reagent or solvents from the reservoir 198 by the gas pressure therein. The inert gas supply line 202 of each reservoir 198 receives pressurized inert gas from the source 28 through a pressure regulator 56 or 106 and a solenoid valve 58 or 108. The release of gas through the vent conduit 206 is likewise controlled by one of the solenoid valves 62 or 110 and one of the flow regulators 64 or 111. The flow of liquid reagent or solvent through the conduit 208 is controlled by one of the valves 66 or 112. Each time one of the liquid reagents or solvents is to be delivered to the reaction chamber or the conversion flask 14, the corresponding argon supply valves and vent valves are opened to establish a dynamic equilibrium condition within the particular reservoir. Reagent or solvent in liquid form can then be introduced by opening the valve in the conduit 208 and the valve 82 to waste trap 60. Liquid is expelled from the reservoir at a constant rate, enabling the quantity of liquid delivered to be accurately controlled by controlling the length of time the valve in the delivery line 208 is held open.

Figure 8:
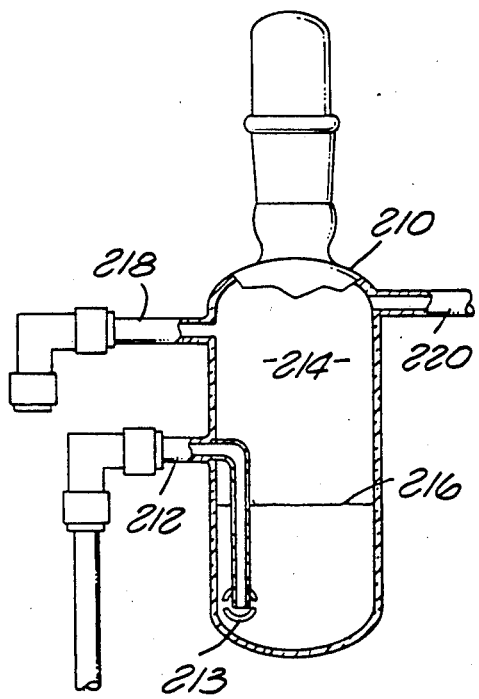
FIG. 8 is a vertical cross-sectional view of a typical reservoir of the present invention for a reagent to be used in the form of a gas or vapor.

A typical reservoir 210 of the present invention for delivery of a reagent in gas or vapor form is illustrated in FIG. 8. An inert gas inlet 212 terminating in a glass frit sparging element 213 is provided for introducing inert gas to the interior 214 of the reservoir 210 at a point adjacent the bottom thereof and substantially below a level 216 of liquid reagent therein. A vent conduit 218 and an output or delivery line 220 communicate with the interior 214 at points above the liquid level 216. The reservoir 210 is typical of the reservoirs 44, 46 and 48 of FIG. 3, with one of the pressure regulators 56 and one of the valves 58 controlling the flow of gas through the conduit 212 from the gas pressure source 28. Likewise, the escape of pressurized gas to the vent conduit 218 is controlled by one of the flow regulators 64 and flow valves 62, and the delivery of reagent along the line 220 is controlled by one of the diaphragm valves 66 in line with a flow meter 74 and flow regulator 76.

Thus, although the reagents $R_2$, $R_3$ and $R_{3A}$ are delivered to the reaction chamber in gas or vapor form, they are stored as liquids and vaporized when needed. Vaporization is accomplished by the bubbling of inert gas upwardly through the liquid reagent. In this way, the inert gas in the interior 214 of the reservoir 210 becomes saturated with reagent vapor. Each time reagent is needed, the valves connected to the conduits 212 and 218 are opened to bubble inert gas through the reagent and establish a dynamic equilibrium condition. The valve 66 within the delivery conduit 220 is then opened for a predetermined length of time to deliver the desired quantity of reagent vapor to the reaction cell. The flow regulator 76 in line with the particular valve 66 causes the vapor to be delivered by the reservoir at a constant rate indicated by the flow meter 74.

FIGS. 9 through 13 illustrate the structure and operation of a valve assembly 222 which embodies the valves 66 and 72 and the continuous manifold 68 of FIG. 3. The valve assembly 222 includes a valve block 224 which is seen most clearly in FIGS. 11 and 12. The valve block 224 is an elongated block of rectangular cross-section having a continuous primary passage 226 in a sawtooth pattern formed by cross-drilling the valve block from a surface 228 thereof. The primary passage 226 is thus a single continuous passage communicating at alternating intersections thereof with a plurality of valving sites 230 on the surface 228 through corresponding openings 232. A tapered connector port 234 communicates with one end of the primary passage 226. A plurality of secondary passages 236 extend from tapered connector ports 238 at the opposite side of the valve block 224 to corresponding openings 240 in proximity to the openings 232 at the respective valving sites 230. The valve block 224 is received within a longitudinal slot 242 of a base 244 having a plurality of threaded openings 246 in alignment with the connector ports 234 and 238 for reception of connector fittings 248. The fittings 248 are adapted to compress resilient doubly tapered ferrules 250 against the connector ports 234 and 238, respectively, to sealingly join tubes 252 extending through the ferrules with the various passages of the valve block 224. In this way, the connector port 234 of the primary passage communicates with the inlet passage 36 of the chamber apparatus 12 through the fluid conduit 40 of FIG. 3, and the first seven of the eight secondary passages communicate with the fluid outlets 208 and 220 of the reservoirs 42 through 54 respectively. The secondary passage furthest from the connector port 234 communicates with the inert gas pressure source 28 through the pressure regulator 70 shown in FIG. 3.

The structure of the doubly tapered ferrule connections to the ports of the valve block 224 is shown in greater detail in FIG. 9A, depicting the port 234 by way of example.

The ferrule 250 of FIG. 9A is received at its inner side 243 within the connector port 234 and at its outer side 245 within a tapered recess 247 of the fitting 248, the port 234 and the recess 247 being tapered at angles greater than the angles of taper of the respective sides of the ferrule. The ferrule is preferably tapered at the same angle on both sides, with the port 234 and recess 247 being tapered at an angle three degrees (3°) greater than the ferrule. This fit between differently tapered surfaces focuses the forces of compression upon the tips 249 of the ferrules 250, providing an effective seal with a minimum of pressure on the side of the valve block 244. Excessive pressures on the valve block 224 which can distort the valving sites 230 are thus avoided.

A series of diaphragm retaining blocks 254 are bolted aagainst the surface 228 of the valve block 224 with diaphragms 256 sandwiched therebetween. The upper end of each diaphragm retaining block is threaded to receive an air connector 258 communicating with a recess 260 on the underside thereof and extending generally over one of the valving sites 230. An O-ring 262 may be received within an annular groove surrounding the recess 260 to provide an effective air seal.

The diaphragms 256 are constructed of a substantially chemically inert air-tight material enabling them to be alternately drawn away from and pressed against the valve sites 230 by the application of vacuum and air pressure, respectively, through the fittings 258. The two alternate conditions of the diaphragm 256 are shown in FIGS. 13A and 13B. In the condition of FIG. 13A air or gas pressure applied to the fitting 258 forces the diaphragm 256 against the opening 232 of the primary passage and the opening 240 of the secondary passage at the particular valving site 230. The openings 232 and 240 are thus closed by the diaphragm 256, permitting no communication therebetween. This corresponds to the closed position of the valve located at the particular valving site. In the condition of FIG. 13B, vacuum applied to the connector fitting 258 draws the diaphragm 256 away from the openings 232 and 240, permitting communication between the primary and secondary passage over the surface of the valve block at that point. This corresponds to the open condition of the particular valve, permitting fluid from one of the reservoirs or from the inert gas pressure source 28 to flow through the primary passage 226 to the inlet passage 36.

The novel construction of the valve assembly 222 described above enables reagents and solvents to be delivered to the reaction chamber in accurate amounts with virtually no contamination between the various fluids. The continuity of the primary passage 226 and the connection at one end thereof to the inlet passage of the chamber apparatus 12 are largely responsible for this advantageous operation. Delivery of any one of the seven reagents and solvents can be accomplished by applying a vacuum to one of the diaphragms 256 and positive gas pressure to the others, enabling the desired reagent or solvent to pass into the primary passage 226 and through the fluid conduit 40 to the reaction chamber. When the desired amount of fluid has passed beneath the particular diaphragm, gas pressure is again applied thereto through the fitting 258 so that each of the seven reagent and solvent valves of the assembly 222 is closed. Delivery of the fluid can then be completed by applying a vacuum to the diaphragm associated with the inert gas port at the remote end of the valve block 224 to flush the entire primary passage 226 with inert gas and force the reagent or solvent fluid remaining in the lines into the reaction chamber 34. Because there are no discontinuities or dead-end branches in the primary passage 226, there is no place for any of the reagents or solvents to become trapped between delivery procedures. The reagents and solvents delivered in succeeding sequencing steps are thus as pure as possible, allowing the chemistry within the reaction cell to proceed as intended and without any unnecessary loss of yield due to contaminated reagents or solvents.

The valve assembly 222 is also illustrative of the valve design incorporated in many other portions of the apparatus to minimize contamination whenever a single port must be selectively connected to a plurality of other ports. Thus, the valves 112 and 118 for delivering reagent and solvent to the conversion flask 14 form a valve assembly in combination with the continuous manifold 114, and the valve 78, 80 and 82 for directing fluids from the outlet passage 38 of the chamber apparatus 12 form a similar valve apparatus in combination with the continuous manifold 84. Likewise, the valves for the connection of waste and vacuum to the conversion flask and the fraction collector and the valves controlling flow from the conversion flask to the fraction collector are constructed similarly to the valve assembly 222. The principal difference in each of these valve assemblies is the number of valving sites associated therewith.

It will be understood that, while the manifolds 68, 84 and 114 are illustrated schematically in FIG. 3 as having a series of small discontinuities or branches adjacent each diaphragm valve associated therewith, each of the manifolds is actually a single continuous passage constructed in the manner of the primary passage 226 of FIGS. 11 and 12.

The vacuum and gas pressure for actuating the diaphragm valves between the open and closed conditions are omitted from the schematic diagram of FIG. 3 for purposes of simplicity, and are preferably separate from the source 28 and vacuum pump 90 described herein.

Figure 14:
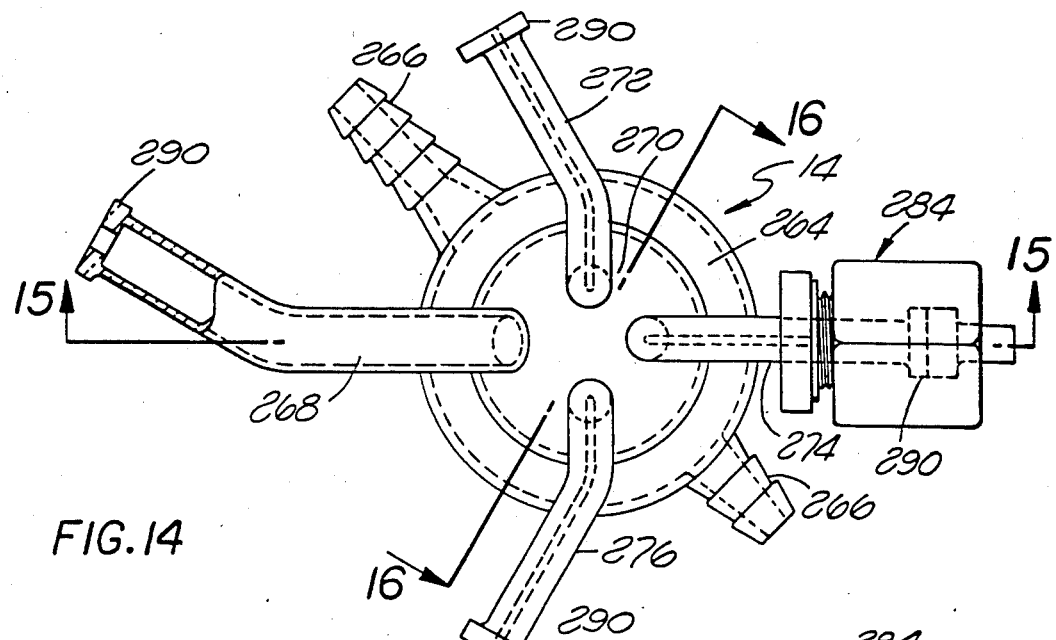
FIG. 14 is a top plan view of a conversion flask constructed in accordance with the present invention.
Figure 15:
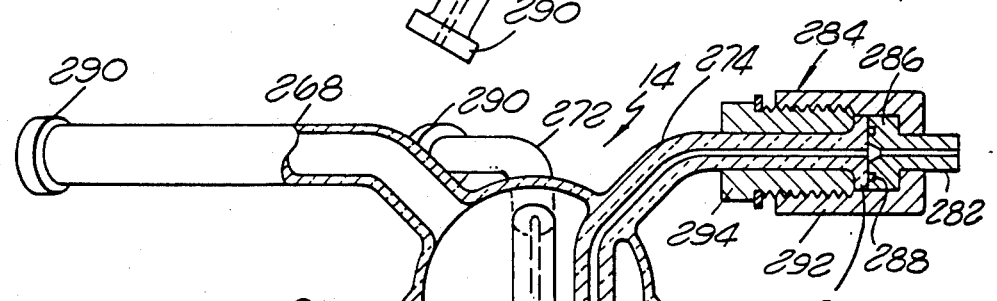
FIG. 15 is a vertical sectional view taken along the line 15—15 of FIG. 14.
Figure 16:
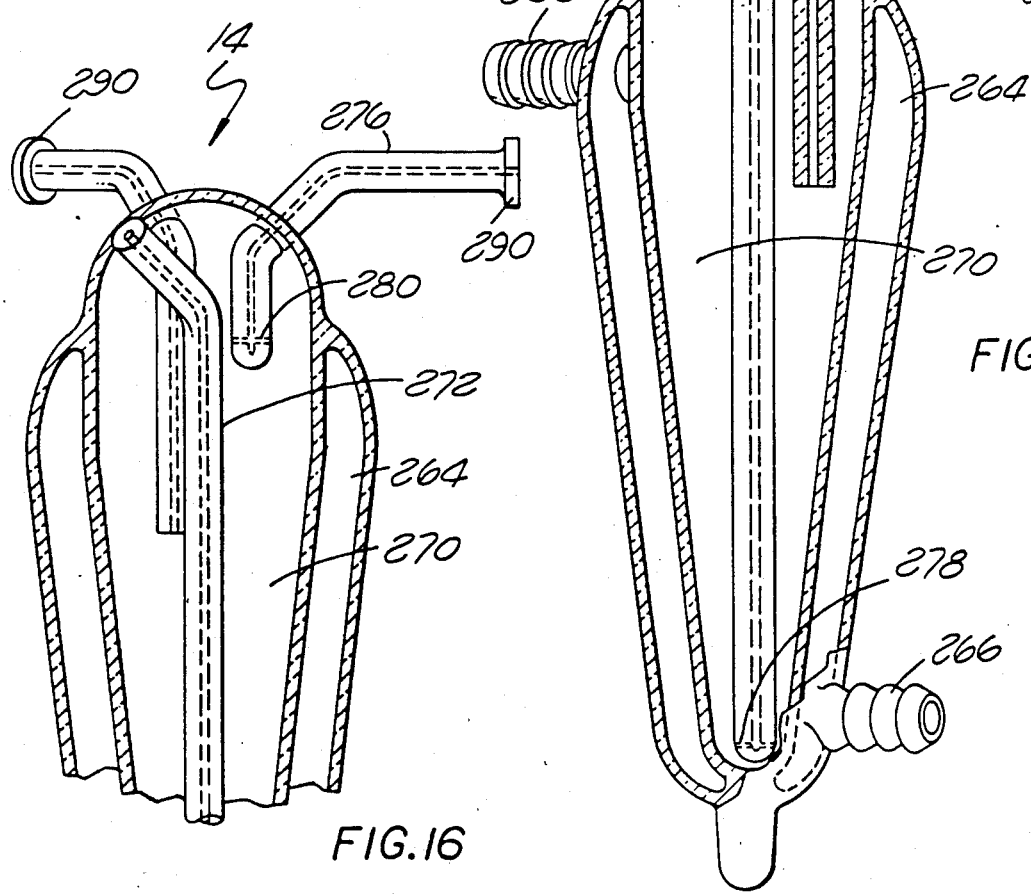
FIG. 16 is a vertical sectional view taken along the line 16—16 of FIG. 14.

The conversion flask 14 is shown in detail in FIGS. 14 through 16. The flask 14 is of the double-walled glass type having a space 264 between the walls for circulation of a heating fluid such as water. The heating fluid is passed to and from space 264 through a pair of nipples 226 adapted to receive standard flexible tubing ends. A large bore tube 268, connectible to the vacuum trap 88 and the vacuum pump 90 through the valve 96 and to the waste trap 60 through the valve 92, communicates with the interior chamber 270 of the flask adjacent its upper end. Capillary tubes 272, 274 and 276 extend through the upper end of the flask to points within the interior chamber 270. The bores of the tubes 272 and 276 are closed at the inner ends thereof and each of the tubes is provided with a plurality of relatively restricted radially spaced orifices 28 or 280 adjacent its inner end.

Due to the relatively small amount of protein or peptide sample for which the apparatus 10 is designed, and the relatively low volumes of reagent and solvent used therein, the conversion flask 14 has a much smaller interior volume than any of the prior flasks known to applicants. The volume of the flask 14 is slightly over one (1) milliliter, while the prior automatic conversion flasks known to applicants have all had volumes of one hundred (100) milliliters.

The fractions cleaved from the sample in the reaction chamber 34 are passed sequentially to the flask 14 through the valve 78 and the capillary 274. Reagents and solvents enter the interior chamber of the flask through the capillary 276, from which they are forced through the restricted orifices 280 as a spray impinging on the walls of the chamber 270 to wash any residue thereon to the bottom of the flask. During the conversion reaction, an inert gas may be introduced through the capillary tube 272 to agitate the liquid and aid in evaporating the solvent therefrom. The gas exits the tube 272 through the restricted orifices 278 as very small bubbles, providing optimal dispersion of the gas through the liquid regardless of the size of the flask and the amount of gas used. When the conversion reaction is complete, the fraction is forced upwardly by positive gas pressure within the flask through the long capillary 272 to the respective vial in the fraction collector 16. This can be accomplished in two aliquots to effect a more complete transferrence of the fraction to the fraction collector 16. The first aliquot, of approximately 200 microliters ($\mu$l), is initially expelled to the fraction collector. Then an additional 50 microliters ($\mu$l) of solvent is introduced to dissolve any residue on the lower walls or bottom of the flask. The second aliquot is then expelled. In this way, a high yield of each fraction can be achieved.

After a particular fraction has been transferred, an additional 750-900 microliters ($\mu$l) of solvent may be introduced to dissolve whatever residue from the previous cycle remains on the upper walls of the flask 14. This additional solvent is then expelled to waste, leaving the flask walls clean.

The outer ends of the tubes 268, 272, 274 and 276 are sealed to respective flexible conduits 282 leading to the various other elements of the apparatus 10 by interfitting screw thread connectors 284. The end of each conduit 282 is provided with a radial flange portion 286 having a resilient O-ring 288 which abuts and seals against the flat ground glass face of a radial flange 290 on one of the glass tubes. An internally threaded collar 292 is slidably positioned over the conduit 282 to receive the glass flange 290 and engage a two-piece externally threaded fitting 294 which is placed about the glass tube. Advancement of the collar 292 over the fitting 294 forces the flange portion 286 against the glass flange 290 to produce an extremely effective seal. The various portions of the connectors 284 may be made of substantially chemically inert materials, such as commercial fluorocarbon polymers, to virtually eliminate the possibility of deterioration and subsequent leakage.

An alternative construction of the flask 14 would eliminate the space 264 and the nipples 266, yielding a single-walled vessel which could be maintained at an elevated temperature by placement in the heated environment 32. This structure would have the advantage of maintaining the entire length of the glass tubes and the connectors 284 at the elevated temperature, minimixing condensation of semi-volatile fluids therein, but would not enable the flask and the chamber 12 to be maintained at different temperatures.

The reagents and solvents used in the apparatus 10 for the sequential degradation of protein or peptide chains are preferably as follows:

$R_1$ phenylisothiocyanate (PITC) (17% solution in heptane)
$R_2$ trimethylamine or triethylamine (25% solution in water)
$R_3$ trifluoroacetic or heptafluorobutyric acid
$R_{3A}$ water vapor
$R_4$ trifluoroacetic acid (25% solution in water)
$R_{4A}$ hydrogen chloride (1N solution in methanol)
$S_1$ benzene
$S_2$ ethyl acetate with 0.1% acetic acid
$S_3$ butyl chloride
$S_4$ acetonitrile or methanol In operation, the various valves and other mechanisms of the apparatus 10 are preferably controlled by the automatic control unit 18 to perform an indefinite number of degradation cycles on a protein or peptide sample without human intervention. The control unit 18 may take the general form of the programming unit disclosed in Penhasi U.S. Pat. No. 3,725,010, with alterations to provide for the particular sequence of steps required by the apparatus 10, or may be a more sophisticated electronic control in the nature of a special or general purpose digital computer. Alternatively, the various steps in each degradation cycle can be performed manually by an operator according to a predetermined schedule to achieve the same results.

Prior to commencing the degradation process, a sample of the protein or peptide being investigated must be mounted to an appropriate sample support surface. The matrix material is first applied to the support surface, with the sample later embedded therein, as described in Examples 1 and 2 below. When the element 190 or 190' is used as a sample support surface, it is placed between the chamber elements 134 and 146 along with at least one of the sealing sheets 194 such that the element 190 is received within the reaction chamber 34 at the location of the recess 192. In the preferred embodiment of the present invention, a pair of sealing sheets 194 are used, sandwiching the element 190 therebetween. The chamber elements 134 and 136 are then inserted into the sleeve 132 and assembled with the various other components to form the chamber apparatus 12.

When the sample-containing films is to be carried by the interior surface of the chamber 34' or the chamber 324, it is applied thereto as described in Example 2 below.

The chamber elements are initially assembled within the sleeve 132 and held in place by the cap 160. In the case of the chamber 34', the annular sheet of yielding material 316 is positioned between the chamber elements 134' and 136' upon assembly. The solid matrix material and the sample are then applied to the walls of the chamber 34' or 324, as described in Example 2, and the sleeve 132 is assembled with the other components to form a complete apparatus.

The reaction chamber 34 and the associated fluid conduits may be initially evacuated by opening the valve 82 to the vacuum trap 88 and vacuum pump 90, in preparation for the sequential introduction of reagents $R_1$ through $R_{34}$, solvents $S_1$ through $S_3$ and inert gas from the source 28. Each time one of the reagents or solvents is to be introduced, the corresponding inert gas supply valve 58 and vent valve 62 are opened to pressurize the particular reservoir and establish a dynamic equilibrium condition therein. Inert gas is thus introduced and released from the reservoir simultaneously to maintain a constant pressure within the reservoir. In the case of the reservoirs 44, 46 and 48, the flow of saturated gas therefrom during delivery is controlled by one of the flow regulators 76.

Once the reservoir containing the particular reagent or solvent to be delivered is pressurized and placed in equilibrium as described above, a vacuum is applied by the auxiliary vacuum source (not shown) to the diaphragm of the corresponding flow valve 66 to open the valve and produce a flow of the reagent or solvent through the continuous manifold 68 and the conduit 40 to the chamber inlet passage. The valve 66 is held open a predetermined length of time to allow precisely the desired amount of reagent or solvent to pass, and is then closed by the application of gas pressure to the diaphragm thereof. Vacuum from the auxiliary vacuum source is then applied to the diaphragm of the valve 72 at the remote end of the continuous manifold 68 to flush the manifold of any remaining reagent or solvent and complete delivery thereof to the chamber. The valve 72 is then closed by the application of positive pressure to the diaphragm thereof, leaving the manifold 68 free to solvent and reagent in preparation for the next delivery step.

The diaphragm valve 80 is generally held open during passage of the various reagents and solvents through the chamber 34 to conduct the effluent therefrom through the chamber outlet passage and the manifold 84 to the waste trap 60. After delivery of a particular reagent or solvent, the chamber and the associated conduits can be evacuated by opening the diaphragm valve 82 to the vacuum pump 90. Alternatively, the chamber and the sample therein can be dried at the appropriate times by passing inert gas through the chamber by way of the valve 72. The gas exiting the chamber can then be passed to the waste trap 60, or if desired, drawn out by the vacuum pump 90 to accelerate the drying process.

After completion of the coupling and cleaving steps, the extraction solvent $S_3$ is delivered to the reaction chamber 34 to dissolve the cleaved amino acid derivative produced during the particular cycle of degradation and to deliver the solution to the conversion flask 14 through the conduit 86. For this purpose, the valve 78 is open and the valves 80 and 82 remain closed. The conversion reagents $R_4$ and $R_{4A}$ (if used) and solvent $S_4$ may then be delivered to the conversion flask 14 at the appropriate times by opening the corresponding valves 112 to pass the liquids through the manifold 114 and the conduit 104 to the conversion flask. Each delivery is preceded by the pressurization and venting operations described above in relation to delivery of the other reagents and solvents, and followed by opening the valve 118 to purge the manifold 114 and the conduit 104.

The fraction transferred to the conversion flask 14 is the anilinothiazolinone derivative of the N-terminal amino acid of the protein or peptide sample and is converted automatically during the next coupling and cleavage cycles of the reaction chamber 34 to the more stable phenylthiohydantoin amino acid, partly according to the articles noted above by Wittmann-Liebold. Briefly, the amino acid fraction within the conversion flask may first be evaporated by passage of inert gas over the solution through the short capillary 276 and bubbling of inert gas through the liquid by way of the capillary 272, followed by application of vacuum through the tube 268. The conversion reagent $R_4$ may then be introduced through the capillary 276 by way of the conduit 104 and one of the valves 112 (see FIG. 3) in the desired quantity. Rapid evaporation of the conversion flask after the desired conversion time may be accomplished by simultaneously applying vacuum to the conversion flask through the tube 268 and inert gas through capillaries 272 and 276. In order to further stabilize the acidic side chains of Pth-aspartic and Pth-glutamic acids, one can further dissolve the residue in the conversion flask by introduction of reagent $R_{4A}$ through the capillary 276 by way of the conduit 104 and one of the valves 112 in the desired quantity. Evaporation of the conversion flask is again accomplished by applying vacuum through the tube 268 and inert gas through capillaries 272 and 276. The Pth-amino acid remaining within the conversion flask is then redissolved in the solvent $S_4$ introduced through the conduit 104 for transfer of the fraction to the appropriate vial in the fraction collector 16. The transfer of the fraction is accomplished by opening the valve 131 connected to the long central capillary 272 of the conversion flask and admitting pressurized inert gas through the capillary 276 to force the fraction from the flask.

The vial carrousel of the fraction collector 16 is rotated through a predetermined angle once during each degradation cycle, such that each incoming fraction is collected in a separate vial. At an appropriate point in the degradation cycle, the fractions within the fraction collector may be further dried by opening the valve 98 to vacuum or opening the valves 128 and 94 to pass inert gas from the source 29 over the fractions and finally to the waste trap 60.

The various components of the apparatus 10 are preferably constructed of materials which are substantially inert and are highly resistant to deterioration. Such materials include borosilicate glass, certain fluorocarbon polymers, and, in some cases, stainless steel and aluminum. The sealing structures and other elements of the apparatus 10 have been designed such that they can be manufactured almost exclusively from these materials. It is felt that the resulting apparatus is the cleanest and most contamination-free system obtainable and would function in that condition indefinitely.

The various steps performed by the apparatus 10 in a typical degradation and conversion cycle are listed in Table 1. The duration of each step and the functional state of the apparatus during each step are also given. The functions shown correspond to the conditions of the various valves of the apparatus, and the marks in the columns signify when the appropriate valves are open. For example, the columns "$R_1$", "$R_2$", "$R_3$", "$R_{3A}$", "$S_1$", "$S_2$" and "$S_3$" denote the conditions of the various pairs of valves 58 and 62 for selectively pressurizing and establishing a dynamic equilibrium condition within the reservoirs 42 through 54. Wherever a mark appears in one of these columns, the valves 58 and 62 associated with the particular reservoir are open, either in preparation for or during delivery of the particular reagent or solvent to the reaction chamber. The valves remain closed at all other times. Likewise, the "argon" column shows the condition of the valve 72 for delivery of an inert gas such as argon to the reaction chamber through the manifold 68, the "deliver" column shows the condition of the valve 66 corresponding to any reservoir which is pressurized at the time, and the columns labeled "waste", "collect" and "vacuum", show the conditions of the valves 82, 78 and 80, respectively. As described above, each step of solvent or reagent delivery is preceded by pressurization of the appropriate solvent or reagent reservoir and followed by the introduction of inert gas through the valve 72 to complete delivery of the solvent or reagent and flush the delivery lines.

The columns "$R_4$", "$R_{4A}$" and "$S_4$" denote the conditions of the various pairs of valves 108 and 110 for selectively pressurizing and establishing a dynamic equilibrium within the reservoirs 100 through 102, and the "deliver/argon" column signifies the condition of both the valve 122 which admits inert gas into the conversion flask through the line 124 and the valve 112 corresponding to the reservoir which is pressurized at the time. The columns "argon", "waste 1", "vacuum", "collect" and "waste 2" show the conditions of the valves 118, 92, 96, 131 and 125, respectively.

Of the fraction collector functions listed, the columns "argon", "waste" and "vacuum" show the conditions of the valves 128, 94 and 98, respectively.

With the exceptions noted hereinabove, the sequence of steps listed in Table 1 essentially conforms to the Edman degradation processes described in the cited publications and will not be discussed in detail. Any deviations from general practice will be clear from the names of the steps and the corresponding functional states tabulated in Table 1.

In practice, the following variations of the sequencing program of Table 1 may be implemented to adapt the program to the needs of a particular user:

(1) Steps 18 through 58 can be looped one or two times on the first sequencer cycle to insure complete coupling of all amino groups on the protein.

(2) Step 65 can be followed by a 20 to 60 second delivery of water vapor ($R_{3A}$) through the reaction chamber to reduce dehydration of side chains of serine and threonine.

(3) Step 65 can be followed by delivery of 0.05 ml of 1N hydrochloric acid in methanol ($R_{4A}$) to the conversion flask to methylate the side chains of aspartic acid and glutamic acid. If this is done, $S_4$ if preferably methanol.

(4) Step 76 can be followed by delivery of 0.7 to 1 ml of $S_4$ (acetonitrile or methanol) that is subsequently delivered to waste to thoroughly clean the conversion flask.

(5) Step 8 can be increased in duration (500 to 1000 seconds) to promote cleavage of amino terminal proline residues.

The nature of the present invention will be further clarified by the following specific examples of the practice of the invention. It should be understood that the data disclosed serve only as examples of processes which have been performed with the apparatus and method of the present invention and are not intended to limit the scope of the invention.

The amino acid sequences set forth in the following examples are tabulated in the one-letter amino acid code, which is defined as follows:

| | |
|---|---|
| A - alanine | L - leucine |
| R - arginine | K - lysine |
| N - asparagine | M - methionine |
| D - aspartic acid | F - phenylalanine |
| C - cysteine | P - proline |
| E - glutamic acid | S - serine |
| Q - glutamine | T - threonine |
| G - glycine | W - tryptophan |
| H - histidine | Y - tyrosine |
| I - isoleucine | V - valine |

EXAMPLE 1

A solid matrix of polymeric quaternary ammonium salt, suitable for embedding a protein sample for sequencing, can be prepared on the fibrous sheet element 190 and 190' described above, and a protein sample can be embedded in the matrix as follows:

A glass fiber disc, 12 mm in diameter and 0.25 to 0.5 mm thick, is cut from a sheet of glass microfiber filter which is available commercially from Whatman, Inc., Clifton, N.J. The disc is placed in the depression 192 of the chamber element 134. 25 microliters of an aqueous solution containing 1.5 mg of 1,5-dimethyl-1,5-diazaundecamethylene polymethobromide and 0.0033 mg of glycylglycine is dropped onto the glass fiber disc from a syringe or pipette. The water is evaporated under vacuum or by heating in a stream of warm nitrogen. The remainder of the chamber apparatus 12 is assembled and installed in the apparatus 10. The protein sequencing program is initiated at step 18, and 4 to 6 complete degradation cycles are accomplished in order to remove impurities from the 1,5-dimethyl-1,5-diazaundecamethylene polymethobromide that might react chemically with the protein sample or otherwise interfere with the Edman process. The chamber apparatus 12 is partially disassembled and 25 microliters of a solution of the protein is dropped onto the glass fiber disc.

The protein solution dissolves the 1,5-dimethyl-1,5-diazaundecamethylene polymethobromide and the liquid is removed by evaporation to leave behind a thin film of 1,5-dimethyl-1,5-diazaundecamethylene polymethobromide with the protein sample embedded therein. If the initial protein sample volume is greater than 25 microliters, the sample can be applied in 25 microliter aliquots with the liquid being removed by evaporation between aliquot applications. The chamber apparatus 12 is reassembled and reinstalled in the apparatus 10. The protein sequencing program is then initiated at step 18 and carried through as many degradation cycles as desired.

EXAMPLE 2

A solid matrix of polymeric quaternary ammonium salt, suitable for embedding a protein sample for sequencing, can be prepared on the interior walls of a glass capillary vessel, and a protein sample can be embedded in the matrix as follows:

The chamber element 324 or the chamber elements 134' and 136' are initially assembled with the sleeve 132 and the cap 160, as illustrated in the figures, to form a compact cartridge subassembly which is easily manipulated for introduction of the matrix and the sample. The sub-assembly is held horizontally and 10 microliters of an aqueous solution containing 0.6 mg of 1,5-dimethyl-1,5-diazaundecamethylene polymethobromide and 0.0013 mg of glycylglycine is injected into the reaction chamber from a syringe.

The chamber 320 is preferably constructed to have a diameter of 1/16" at its two ends and a diameter of ⅛" at its middle, producing a chamber which will accommodate up to 25 microliters (ul) of solution in the horizontal condition without spilling out at the ends. This configuration of the chamber 324 holding a solution in the horizontal condition is illustrated in FIG. 18B, with the sleeve 132 and related structure omitted for simplicity. The sub-assembly is then rotated about its axis while the liquid in the reaction chamber is evaporated by directing a stream of air or nitrogen through the chamber, leaving a thin film of 1,5-dimethyl-1,5-diazaundecamethylene polymethobromide on the chamber walls. The sub-assembly is then installed in the apparatus 10, the protein sequencing program is initiated at step 18, and 4 to 6 complete degradation cycles are accomplished. The sub-assembly is next removed from the apparatus 10 and held horizontally while 10 microliters of the protein solution is dropped into the reaction chamber from a syringe. The sub-assembly is again rotated about its axis while the liquid in the reaction chamber is evaporated by a stream of nitrogen directed through the chamber, leaving a thin film of 1,5-dimethyl-1,5 diazaundecamethylene polymethobromide with the protein sample embedded therein as illustrated in FIG. 18C. The sub-assembly is then reinstalled in the apparatus 10 and the protein sequencing program is initiated at step 18 and carried through as many degradation cycles as desired.

EXAMPLE 3

Angiotensin, 0.0005 mg, contained in 25 microliters of aqueous 20% formic acid was embedded in a solid matrix of precycled 1,5-dimethyl-1,5-diazaundecamethylene polymethobromide according to the method of Example 1. The angiotension was subjected to eight cycles of Edman degradation, and the phenythiolhydantoin amino acids produced at each cycle were analyzed by high pressure liquid chromatography according to the method described in Johnson et al, "Analysis of Phenylthiohydantoin Amino Acids by High Pressure Liquid Chromatography on Du Pont Zorbax CN Columns", Anal. Biochem. 100, 335 (1979). The following sequence, listed below as "Experimental," was obtained. The known sequence is also listed below for comparison.

```
                 1       3       5       7
Experimental:    D—R—V—Y—I—H—P—F
Known:           D—R—V—Y—I—H—P—F
```

This result is significant because it demonstrates that even small peptides can be sequenced in the manner of the present invention. The ability to sequence small peptides stems from the fact that the sample is embedded in a film for retention, rather than being adsorbed directly onto a support surface, and therefore can be held securely regardless of size. Whereas sorptive bonds comprise a large number of non-covalent interactions between the sample and the surface and are heavily dependent on the size of the molecules, the holding power of the film disclosed herein is relatively unaffected by sample size.

EXAMPLE 4

Sperm whale apomyoglobin, 0.01 mg, contained in 25 microliters of aqueous 20% acetic acid was embedded in a solid matrix of precycled 1,5-dimethyl-1,5-diazaundecamethylene polymethobromide according to the method of Example 1. The apomyoglobin was subjected to 40 cycles of Edman degradation, and the phenylthiohydantoin amino acids were analyzed according to the method of Example 3 to give the sequence listed below as "Experimental." The known sequence of sperm whale apomyoglobin is also listed below for comparison.

```
               1           5           10          15  16          20
Experimental:  V—L—S—E—G—E—W—Q—L—V—L—H—V—W—A—K—V—E—A—D—V—A—G—H—
Known:         V—L—S—E—G—E—W—Q—L—V—L—H—V—W—A—K—V—E—A—D—V—A—G—H—

25          30          35          40
               —G—Q—D—I—L—I——R—L—F—K—S—H—P—E—T—L—
               —G—Q—D—I—L—I—R—L—F—K—S—H—P—E—T—L—
```

EXAMPLE 5

A Drosophila malanogaster larval cuticle protein of previously unknown structure, 0.01 mg, contained in 25 microliters of an aqueous solution of 0.1% sodium dodecyl sulfate and 0.05M ammonium bicarbonate, was embedded in a solid matrix of precycled 1,5-dimethyl-1,5-diazaundecamethylene polymethobromide according to the method of Example 1. The cuticle protein was subjected to 36 cycles of Edman degradation, and the phenylthiohydantoin amino acids were analyzed according to the method of Example 3 to give the sequence listed below as "Experimental."

```
          1                   5
Experimental: N—A—N—V—E—V—K—E—L—V—

11         15              21
       —N—D—V—Q—P—D—G—F—V—S—K—L—V—L—

25            31          35
            —D—D—G—S—A—S—S—A—T—G—D—I—
```

EXAMPLE 6

A Drosophila malanogaster larval cuticle protein of previously unknown structure, 0.005 mg, contained in 10 microliters of an aqueous solution of 0.1% sodium dodecyl sulfate and 0.05M ammonium bicarbonate, was embedded in a solid matrix of precycled 1,5-dimethyl-1,5-diazaundecamethylene polymethobromide according to the method of Example 2. The cuticle protein was subjected to 24 cycles of Edman degradation, and the phenylthiohydantoin amino acids were analyzed according to the method of Example 3 to give the sequence listed below as "Experimental."

```
          1                   5
Experimental: N—A—N—V—E—V—K—E—L—V—

11         15              21
       —N—D—V—Q—P—D—G—F—V—S—K—L—V—L—
```

The results achieved in Examples 5 and 6 demonstrate that the apparatus and method of the present invention is suitable for sequencing proteins and peptides dissolved in a solution of sodium dodecyl sulfate (hereinafter "SDS"), a potent anionic detergent. This is important because the most general method of isolating small quantities of medium to large proteins or peptides for analysis, known as polyacrylimide gel electrophoresis, produces samples in a solution of SDS. This common detergent causes samples to wash out of devices which rely upon adsorptive bonding of the sample to a support surface, however, the solid matrix of the present invention is unaffected by the presence of SDS.

From the above, it can be seen that there has been provided an improved apparatus and method for the sequential performance of chemical processes on a sample of very small size through the use of minimum amounts of reagents and solvents and relatively short cycle times.

The appended claims are intended to cover all variations and adaptations falling within the true scope and spirit of the present invention.

We claim:

1. A sequenator apparatus for use in the determination of the linear sequence of amino acid units in proteins and peptides, comprising:
   chamber means having an interior surface defining a reaction chamber, said chamber having an inlet and an outlet and including a solid, fluid-non-retaining support means within said chamber means;
   a plurality of reservoirs containing fluids, at least some of said fluids being interactable with proteins or peptides to perform the degradation process thereof, said reservoirs being in fluid communication with said reaction chamber,
   pressure means for moving said fluids from said reservoirs to said reaction chamber,
   means for sequentially conducting a plurality of fluids from said reservoirs to said reaction chamber, and through said reaction chamber from said inlet to said outlet in a pressurized stream;
   a highly viscous matrix having semisolid properties comprising a thin film on said solid support means which matrix is located within said reaction chamber, said matrix being permeable to said plurality of fluids by diffusion and absorption of a portion of said fluids into said matrix but said matrix being insoluble in said fluids; and
   a sample of protein or peptide embedded within said matrix;
   whereby said sample is immobilized within said matrix but is exposed to each of the plurality of fluids passing through the reaction chamber for chemical interaction therewith, said exposure being effected by diffusion of a portion of said fluids into the matrix.

2. Apparatus according to claim 1 wherein said matrix comprises a non-reactive polymer.

3. Apparatus according to claim 1 which further comprises means for automatically controlling the functioning of the apparatus through a plurality of cycles.

4. Apparatus according to claim 1 which further includes:
   a conversion flask having a plurality of capillary tubes extending into the interior thereof; and
   means for introducing various fluids into and withdrawing various fluids from said flask through said capillary tubes, including at least one of said plurality of fluids passed to the outlet of the reaction chamber;
   one of said capillary tubes terminating at a point adjacent the bottom of the flask in an inner end at which the bore is closed, said inner end being provided with a plurality of restricted radially spaced orifices;
   such that passage of a gas inwardly through said one capillary tube introduces a plurality of small bubbles into any liquid within the flask, said bubbles serving to uniformly agitate or accelerate drying of any liquid within the flask.

5. Apparatus according to claim 1 wherein the sample is a protein or polypeptide which is to be sequentially degraded to determine the sequence of amino acid units therein.

6. Apparatus according to claim 1 which further includes:
   a conversion flask having a plurality of capillary tubes extending into the interior thereof; and
   means for introducing various fluids into and withdrawing various fluids from said flask through said capillary tubes, including at least one of said plurality of fluids passed to the outlet of the reaction chamber;
   at least one of said capillary tubes having an inner end at which the bore is closed and which is provided with a plurality of restricted radially spaced orifices;
   such that passage of fluid inwardly through said at least one capillary tube produces a spray onto interior walls of the flask to wash down said interior walls.

7. Apparatus according to claim 6 wherein said capillary tubes comprise glass tubes.

8. Apparatus according to claim 1 wherein said matrix comprises a polymeric quaternary ammonium salt.

9. Apparatus according to claim 8 wherein said polymeric quaternary ammonium salt comprises 1,5-dimethyl-1,5-diazaundecamethylene polymethobromide.

10. Apparatus according to claim 8 wherein said polymeric quaternary ammonium salt comprises poly(N,N-dimethyl-3-5-dimethylene piperidinium chloride).

11. Apparatus according to claim 1 wherein said means for sequentially passing a plurality of fluids through said reaction chamber comprises at least one valve means for controlling the flow of said fluids between the reaction chamber and the plurality of reservoirs, said at least one valve means comprising:
  valve block means having a plurality of substantially flat valving sites on a surface thereof, said valve block means defining a plurality passage continuous between two ends thereof and communicating through primary openings with each of said valving sites, and a plurality of secondary passages each communicating through a secondary opening with one of said valving sites;
  a plurality of resilient, substantially impermeable diaphragms covering said respective valving sites, each of said diaphragms being actuable between a first sealing position in which it is forced against one of said valving sites to close the primary and secondary openings communicating with said site and a second position in which it is drawn away from said site to provide a fluid flow path between said primary and secondary openings over the exterior of said valve block means; and
  means for operatively connecting said primary and secondary passages to said plurality of reservoirs and said reaction chamber;
  whereby fluid flow between said plurality of reservoirs and said reaction chamber can be selectively controlled.

12. Apparatus according to claim 11 wherein said connecting means includes a connector fitting at one of said ends of the primary passage such that the primary passage serves as a manifold which can be flushed by a flow of fluid between the connector fitting and a secondary passage furthest away from the connector fitting.

13. Apparatus according to claim 12 wherein said primary passage comprises a plurality of straight passages connected end to end to form a conduit having a sawtooth configuration and communicating at alternating intersections thereof with said respective valving sites.

14. Apparatus according to claim 11 wherein said connecting means comprises at least one tapered ferrule tightly fitted in sliding engagement over a tubing member and urged against a differently tapered recess in said valve block means communicating with one of said passages, such that an inward force applied to said ferrule is focused on a realtively small area of contact between the ferrule and the recess to produce a fluid seal therebetween.

15. Apparatus according to claim 14 wherein said recess is tapered at a greater angle than said ferrule.

16. Apparatus according to claim 14 wherein said ferrule is tapered on opposite sides, one of said sides being urged against said tapered recess by screw thread means having a separate tapered recess for reception of the other side of said ferrule, and recesses being tapered at angles greater than the angles of taper of the corresponding sides of said ferrule.

17. The apparatus of claim 1 wherein said reaction chamber comprises a pair of abutting chamber elements having first and second cavities, respectively, on opposed mating surfaces thereof, said first and second cavities being aligned with each other to form said reaction chamber, said first and second cavities being tapered in directions away from said mating surfaces to locations at which they communicate with said inlet and outlet, respectively.

18. The apparatus of claim 17 wherein said solid support means is a porous sheet positioned within a recess in at least one of said mating surfaces for retention within said reaction chamber in an orientation substantially separating said first and second cavities, said reaction chamber further including a sheet of yielding material located on at least one side of said porous sheet, said sheet of yielding material being sandwiched between said mating surfaces forming a seal therebetween, said sheet of yielding material being permeable to said plurality of fluids.

19. Apparatus according to claim 18 wherein said porous sheet extends substantially transversely across said reaction chamber.

20. Apparatus according to claim 18 wherein said porous sheet is made of a plurality of fibers.

21. Apparatus according to claim 18 wherein said porous sheet is made of a plurality of glass fibers.

22. Apparatus according to claim 18 wherein at least one of said chamber elements includes a raised portion on the mating surface thereof which extends about the cavity therein for comprising said sheet of yielding material against the mating surface of the other chamber element and thus enhancing said seal therebetween.

23. Apparatus according to claim 17 wherein said inlet and outlet comprise a pair of capillary passages extending through said chamber elements and communicating at inner ends with said reaction chamber on opposite sides of the solid support means which solid support means comprises a porous sheet.

24. Apparatus according to claim 23 wherein said capillary passages are coaxial with said reaction chamber and extend therefrom to outer capillary openings in said chamber elements.

25. Apparatus according to claim 23 wherein said chamber elements are of glass and have substantially flat surfaces adjacent said capillary passages.

26. Apparatus according to claim 23 wherein said means for sequentially conducting fluids through the reaction chamber comprises at least one slug of resilient material having a substantially flat sealing end and an axial capillary passage which terminates in an opening at said sealing end, and screw thread means for urging said sealing end axially against one of said capillary passages, such that the axial passage in the slug communicates with said capillary passage and the sealing end of the slug seals against a substantially flat surface of the chamber element adjacent thereto.

27. Apparatus according to claim 26 wherein said at least one slug of resilient material comprises a mass of a fluorocarbon polymer encased in a metallic sleeve.

28. Apparatus according to claim 27 wherein said screw thread means includes a bore for closely receiving said metallic sleeve in an axially sliding relationship to ensure accurate alignment of the passage in the slug with said one capillary passage.

* * * * *